(12) United States Patent
Graham et al.

(10) Patent No.: US 10,548,910 B2
(45) Date of Patent: Feb. 4, 2020

(54) AMIDO-SUBSTITUTED PYRIDOTRIAZINE DERIVATIVES USEFUL AS HIV INTEGRASE INHIBITORS

(71) Applicant: Merck Sharp & Dohme Corp., Rahway, NJ (US)

(72) Inventors: Thomas H. Graham, Quincy, MA (US); Tao Yu, Edison, NJ (US); Sherman T. Waddell, Westfield, NJ (US); John A. McCauley, Maple Glen, PA (US); Andrew Stamford, Chatham, NJ (US); Wensheng Liu, Edison, NJ (US); Jay A. Grobler, Gwynedd, PA (US); Libo Xu, Bridgewater, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 15/775,966

(22) PCT Filed: Nov. 11, 2016

(86) PCT No.: PCT/US2016/061456
§ 371 (c)(1),
(2) Date: May 14, 2018

(87) PCT Pub. No.: WO2017/087257
PCT Pub. Date: May 26, 2017

(65) Prior Publication Data
US 2018/0325927 A1 Nov. 15, 2018

Related U.S. Application Data

(60) Provisional application No. 62/256,403, filed on Nov. 17, 2015.

(51) Int. Cl.
| | | |
|---|---|---|
| *A61K 31/675* | (2006.01) | |
| *A61P 31/18* | (2006.01) | |
| *A61K 31/683* | (2006.01) | |
| *A61K 31/34* | (2006.01) | |
| *A61K 31/426* | (2006.01) | |
| *A61K 31/44* | (2006.01) | |
| *A61K 31/513* | (2006.01) | |
| *A61K 31/52* | (2006.01) | |
| *A61K 31/535* | (2006.01) | |
| *A61K 31/7068* | (2006.01) | |

(52) U.S. Cl.
CPC ......... *A61K 31/675* (2013.01); *A61K 31/683* (2013.01); *A61P 31/18* (2018.01); *A61K 31/34* (2013.01); *A61K 31/426* (2013.01); *A61K 31/44* (2013.01); *A61K 31/513* (2013.01); *A61K 31/52* (2013.01); *A61K 31/535* (2013.01); *A61K 31/7068* (2013.01); *A61K 2300/00* (2013.01)

(58) Field of Classification Search
CPC .................................................... A61K 31/675
See application file for complete search history.

(56) References Cited

U.S. PATENT DOCUMENTS

| | | |
|---|---|---|
| 7,858,788 B2 | 12/2010 | Yoshida et al. |
| 2012/0108564 A1 | 5/2012 | Miyazaki et al. |
| 2014/0221378 A1 | 8/2014 | Miyazaki et al. |

FOREIGN PATENT DOCUMENTS

| | | |
|---|---|---|
| WO | 2014099586 A1 | 6/2014 |
| WO | 2015089847 A1 | 6/2015 |
| WO | 2015095258 A1 | 6/2016 |
| WO | 2016094197 A1 | 6/2016 |
| WO | 2016154527 A1 | 9/2016 |
| WO | 2017087256 A1 | 5/2017 |
| WO | 2017106071 A1 | 6/2017 |

OTHER PUBLICATIONS

Wolff et al. (1997).*
Banker et al. (1995).*
International Search Report and Written Opinion for PCT/US2016/061456, dated Mar. 22, 2017; 10 pages.
Supplementary European Search Report for 16866886.1 dated Apr. 29, 2019, 5 pages.

* cited by examiner

*Primary Examiner* — Paul V Ward
(74) *Attorney, Agent, or Firm* — Nicole M. Beeler; John C. Todaro

(57) ABSTRACT

The present invention relates to Amido-Substituted Pyridotriazine Derivatives of Formula (I): (I) and pharmaceutically acceptable salts thereof, wherein B, X, Y, R, $R^1$, $R^2$ and $R^{10}$ are as defined herein. The present invention also relates to compositions comprising at least one Amido-Substituted Pyridotriazine Derivative, and methods of using the Amido-Substituted Pyridotriazine Derivatives for treating or preventing HIV infection in a subject.

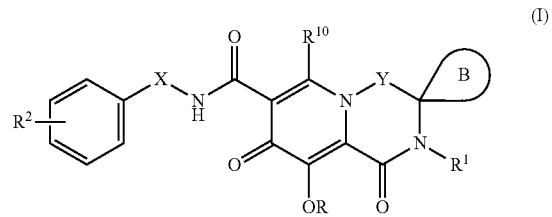

16 Claims, No Drawings

AMIDO-SUBSTITUTED PYRIDOTRIAZINE DERIVATIVES USEFUL AS HIV INTEGRASE INHIBITORS

CROSS REFERENCE TO RELATED APPLICATIONS

This application is a U.S. National Phase application under 35 U.S.C. § 371 of PCT Application No. PCT/US2016/061456 filed Nov. 11, 2016, which claims priority from U.S. Ser. No. 62/256,403 filed Nov. 17, 2015.

FIELD OF THE INVENTION

The present invention relates to Amido-Substituted Pyridotriazine Derivatives, compositions comprising at least one Amido-Substituted Pyridotriazine Derivative, and methods of using the Amido-Substituted Pyridotriazine Derivatives for treating or preventing HIV infection in a subject.

BACKGROUND OF THE INVENTION

A retrovirus designated human immunodeficiency virus (HIV), particularly the strains known as HIV type-1 (HIV-1) virus and type-2 (HIV-2) virus, is the etiological agent of the complex disease that includes progressive destruction of the immune system (acquired immune deficiency syndrome; AIDS) and degeneration of the central and peripheral nervous system. A common feature of retrovirus replication is the insertion by virally-encoded integrase of +proviral DNA into the host cell genome, a required step in HIV replication in human T-lymphoid and monocytoid cells. Integration is believed to be mediated by integrase in three steps: assembly of a stable nucleoprotein complex with viral DNA sequences; cleavage of two nucleotides from the 3' termini of the linear proviral DNA and covalent joining of the recessed 3' OH termini of the proviral DNA at a staggered cut made at the host target site. The fourth step in the process, repair synthesis of the resultant gap, may be accomplished by cellular enzymes.

Nucleotide sequencing of HIV shows the presence of a pol gene in one open reading frame [Rather, L. et al., Nature, 313, 277(1985)]. Amino acid sequence homology provides evidence that the pol sequence encodes reverse transcriptase, integrase and an HIV protease [Tohours, H. et al., EMBO J. 4, 1267 (1985); Power, M. D. et al., Science, 231, 1567 (1986); Pearl, L. H. et al., Nature, 329, 351 (1987)]. All three enzymes have been shown to be essential for the replication of HIV.

It is known that some antiviral compounds which act as inhibitors of HIV replication are effective agents in the treatment of AIDS and similar diseases, including reverse transcriptase inhibitors such as azidothymidine (AZT) and efavirenz and protease inhibitors such as indinavir and nelfinavir. The compounds of this invention are inhibitors of HIV integrase and inhibitors of HIV replication.

The following references may be of interest as background:

International Publication Nos. WO 11/045330 and WO 11/121105 disclose macrocyclic compounds having HIV integrase inhibitory activity.

Kinzel et al., *Tet. Letters* 2007, 48(37): pp. 6552-6555 discloses the synthesis of tetrahydropyridopyrimidones as a scaffold for HIV-1 integrase inhibitors.

Ferrara et al., *Tet. Letters* 2007, 48(37), pp. 8379-8382 discloses the synthesis of a hexahydropyrimido[1,2-a] azepine-2-carboxamide derivative useful as an HIV integrase inhibitor.

Muraglia et al., *J. Med. Chem.* 2008, 51: 861-874 discloses the design and synthesis of bicyclic pyrimidinones as potent and orally bioavailable HIV-1 integrase inhibitors.

US2004/229909 discloses certain compounds having integrase inhibitory activity.

U.S. Pat. No. 7,232,819 and US 2007/0083045 disclose certain 5,6-dihydroxypyrimidine-4-carboxamides as HIV integrase inhibitors.

U.S. Pat. Nos. 7,169,780, 7,217,713, and US 2007/0123524 disclose certain N-substituted 5-hydroxy-6-oxo-1,6-dihydropyrimidine-4-carboxamides as HIV integrase inhibitors.

U.S. Pat. No. 7,279,487 discloses certain hydroxynaphthyridinone carboxamides that may be useful as HIV integrase inhibitors.

U.S. Pat. Nos. 7,135,467 and 7,037,908 disclose certain pyrimidine carboxamides that may be useful as HIV integrase inhibitors.

U.S. Pat. No. 7,211,572 discloses certain nitrogenous condensed ring compounds that are HIV integrase inhibitors.

U.S. Pat. No. 7,414,045 discloses certain tetrahydro-4H-pyrido[1,2-a]pyrimidine carboxamides, hexahydropyrimido[1,2-a]azepine carboxamides, and related compounds that may be useful as HIV integrase inhibitors.

U.S. Pat. No. 8,129,385 discloses certain hexahydro-2H-pyrido[1',2':4,5]pyrazino[2,1-b][1,3]oxazine-9-carboxamides, and related compounds that may be useful as HIV integrase inhibitors.

WO 2006/103399 discloses certain tetrahydro-4H-pyrimidooxazepine carboaxmides, tetrahydropyrazinopyrimidine carboxamides, hexahydropyrimidodiazepine carboxamides, and related compounds that may be useful as HIV integrase inhibitors.

US 2007/0142635 discloses processes for preparing hexahydropyrimido[1,2-a]azepine-2-carboxylates and related compounds.

US 2007/0149556 discloses certain hydroxypyrimidinone derivatives having HIV integrase inhibitory activity.

Various pyrimidinone compounds useful as HIV integrase inhibitors are also disclosed in U.S. Pat. Nos. 7,115,601, 7,157,447, 7,173,022, 7,176,196, 7,192,948, 7,273,859, and 7,419,969.

US 2007/0111984 discloses a series of bicyclic pyrimidinone compounds useful as HIV integrase inhibitors.

US 2006/0276466, US 2007/0049606, US 2007/0111985, US 2007/0112190, US 2007/0281917, US 2008/0004265 each disclose a series of bicyclic pyrimidinone compounds useful as HIV integrase inhibitors.

U.S. Pat. Nos. 7,462,608 and 7,649,015 each disclose phosphate and phosphonate substituted heterocycles useful as HIV nNRTI inhibitors and HIV protease inhibitors, respectively.

International Publication No. WO 2015/095258 discloses phosphate and phosphonate substituted heterocycles useful as HIV integrase inhibitors.

SUMMARY OF THE INVENTION

In one aspect, the present invention provides Compounds of Formula (I):

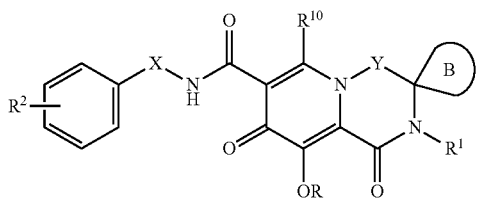

(I)

or a pharmaceutically acceptable salt or prodrug thereof, wherein:

B is $C_3$-$C_7$ cycloalkyl, which may be optionally substituted with one or more groups, each independently selected from $R^6$;

X is $C_1$-$C_3$ alkylene;

Y is —$CH_2$—, —$CH(R^6)$— or —$N(R^3)$—;

R is H or benzyl;

$R^1$ is selected from H, $C_1$-$C_6$ alkyl, $C_3$-$C_7$ cycloalkyl, alkylene)-O—($C_1$-$C_6$ alkyl), ($C_1$-$C_4$ alkylene)-S—($C_1$-$C_6$ alkyl), —($C_1$-$C_4$ alkylene)-$SO_2$—($C_1$-$C_6$ alkyl), ($C_1$-$C_4$ alkylene)-N—($C_1$-$C_6$ alkyl)$_2$, —($C_1$-$C_6$ alkylene)$_m$-Z—($C_1$-$C_3$ alkylene)$_m$-$R^{11}$, $C_1$-$C_6$ haloalkyl, $C_1$-$C_6$ hydroxyalkyl, phenyl, 3 to 8-membered monocyclic heterocycloalkyl and 5 or 6-membered monocyclic heteroaryl;

$R^2$ represents up to 3 optional substitutents, each independently selected from halo, $C_1$-$C_6$ alkyl, —O—($C_1$-$C_6$ alkyl) and $C_1$-$C_6$ haloalkyl;

$R^3$ is selected from H, $C_1$-$C_6$ alkyl, —$SO_2R^4$, —$C(O)R^4$, —($C_1$-$C_6$ alkylene)$_p$-$C(O)N(R^5)_2$, —($C_2$-$C_4$ alkylene)-O—($C_1$-$C_6$ alkyl), —($C_2$-$C_4$ alkylene)-S—($C_1$-$C_6$ alkyl), ($C_2$-$C_4$ alkylene)-$SO_2$—($C_1$-$C_6$ ($C_2$-$C_4$ alkylene)-N—($C_1$-$C_6$ alkyl)$_2$, —($C_1$-$C_6$ alkylene)$_m$-Z—($C_1$-$C_3$ alkylene)$_m$-$R^{11}$, $C_3$-$C_7$ cycloalkyl, phenyl, 4 to 8-membered monocyclic heterocycloalkyl or 6-membered monocyclic heteroaryl and 8 to 10-membered bicyclic heteroaryl;

each occurrence of $R^4$ is independently selected from H, $C_1$-$C_6$ alkyl, $C_1$-$C_6$ haloalkyl, $C_3$-$C_7$ cycloalkyl, phenyl, 3 to 8-membered monocyclic heterocycloalkyl, 5 or 6-membered monocyclic heteroaryl and 8 to 10-membered bicyclic heteroaryl, wherein said $C_3$-$C_7$ cycloalkyl group, said phenyl group, said 3 to 8-membered monocyclic heterocycloalkyl group, said 5 or 6-membered monocyclic heteroaryl group and said 8 to 10-membered bicyclic heteroaryl group may be optionally substituted with one or more groups, each independently selected from $R^6$;

each occurrence of $R^5$ is independently selected from H, $C_1$-$C_6$ alkyl, $C_3$-$C_7$ cycloalkyl, —($C_1$-$C_6$ alkylene)-N($R^7$)$_2$, $C_1$-$C_6$ haloalkyl, —C(O)O($C_1$-$C_6$ alkyl)), —($C_1$-$C_6$ alkylene)$_m$-Z—($C_1$-$C_3$ alkylene)$_m$-$R^{11}$, —($C_1$-$C_6$ alkylene)$_p$-$R^8$ and —($C_1$-$C_6$ alkylene)-O—($C_1$-$C_6$ alkyl);

each occurrence of $R^6$ is independently selected from halo, $C_1$-$C_6$ alkyl, $C_1$-$C_6$ haloalkyl, —($C_1$-$C_6$ alkylene)$_m$-Z—($C_1$-$C_3$ alkylene)$_m$-$R^{11}$, —N($R^{20}$)$_2$, 3 to 8-membered monocyclic heterocycloalkyl, 6 to 10-membered bicyclic heterocycloalkyl, —O—($C_1$-$C_6$ alkyl), —O—($C_6$-$C_{10}$ aryl), —O—($C_1$-$C_6$ alkylene)-O—($C_1$-$C_6$ alkyl), —O—($C_1$-$C_6$ haloalkyl), —O—($C_1$-$C_6$ alkylene)-O—($C_1$-$C_6$ alkylene)-O—($C_1$-$C_6$ alkyl), —$S(O)_2$($C_1$-$C_6$ alkyl), —$NHS(O)_2$—($C_1$-$C_6$ alkyl), —$S(O)_2NH$—($C_1$-$C_6$ alkyl), —OC(O)—($C_1$-$C_6$ haloalkyl), —($C_1$-$C_6$ alkylene)$_p$-C(O)O—($C_1$-$C_6$ alkyl), —($C_1$-$C_6$ alkylene)$_p$-C(O)—($C_1$-$C_6$ alkyl), —($C_1$-$C_6$ alkylene)$_p$-C(O)N($R^7$)$_2$, $C_1$-$C_6$ hydroxyalkyl, —P(O)(O$R^9$)$_2$, and —CN;

each occurrence of $R^7$ is independently selected from H, $C_1$-$C_6$ alkyl, $C_3$-$C_7$ cycloalkyl, $C_1$-$C_6$ haloalkyl, —C(O)O ($C_1$-$C_6$ alkyl), —($C_1$-$C_6$ alkylene)$_m$-Z—($C_1$-$C_3$ alkylene)$_m$-$R^{11}$, —($C_1$-$C_6$ alkylene)$_p$-$R^8$ and —($C_1$-$C_6$ alkylene)-O—($C_1$-$C_6$ alkyl);

each occurrence of $R^8$ is independently selected from H, $C_1$-$C_6$ alkyl, $C_3$-$C_7$ cycloalkyl, 5 or 6-membered monocyclic heteroaryl and 3 to 8-membered monocyclic heterocycloalkyl;

each occurrence of $R^9$ is independently selected from H, $C_1$-$C_6$ alkyl and —($C_1$-$C_6$ alkylene)$_m$-Z—($C_1$-$C_3$ alkylene)$_m$-$R^{11}$;

$R^{10}$ is selected from H, $C_1$-$C_6$ alkyl, $C_3$-$C_7$ cycloalkyl and ($C_1$-$C_4$ alkylene)-O—($C_1$-$C_6$ alkyl);

each occurrence of $R^{11}$ is independently selected from —P(O)(—O$R^{18}$)$_2$,

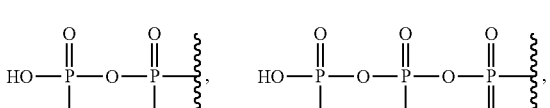

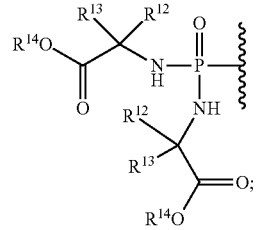

each occurrence of $R^{12}$ is independently selected from H, $C_1$-$C_6$ alkyl, $C_3$-$C_7$ cycloalkyl, phenyl or benzyl, wherein said $C_1$-$C_6$ alkyl may be optionally substituted with a group selected from halo, —O$R^{16}$, —S$R^{16}$, guanidino, —N($R^{16}$)$_2$, —C(O)O$R^{16}$, —C(O)N($R^{16}$)$_2$, —NHC(O)$R^{16}$, 5- or 6-membered monocyclic heteroaryl and 9- or 10-membered bicyclic heteroaryl, and wherein said phenyl group and said benzyl group may be optionally substituted with up to 2 groups, each independently selected from $C_1$-$C_6$ alkyl, halo and —O$R^{16}$;

each occurrence of $R^{13}$ is independently selected from H, $C_1$-$C_6$ alkyl, $C_3$-$C_7$ cycloalkyl, phenyl or benzyl, wherein said $C_1$-$C_6$ alkyl may be optionally substituted with a group selected from halo, —O$R^{16}$, —S$R^{16}$, guanidino, —N($R^{16}$)$_2$, —C(O)O$R^{16}$, —C(O)N($R^{16}$)$_2$, —NHC(O)$R^{16}$, 5- or 6-membered monocyclic heteroaryl and 9- or 10-membered bicyclic heteroaryl, and wherein said phenyl group and said benzyl group may be optionally substituted with up to 2 groups, each independently selected from $C_1$-$C_6$ alkyl, halo and —O$R^{16}$;

each occurrence of $R^{14}$ is independently selected from H, $C_1$-$C_{20}$ alkyl, $C_2$-$C_{20}$ alkenyl, —($C_1$-$C_3$ alkylene)$_m$-($C_3$-$C_7$ cycloalkyl), —($C_1$-$C_3$ alkylene)$_m$-($C_6$-$C_{10}$ aryl) or —($C_1$-$C_3$ alkylene)$_m$-adamantyl, wherein said $C_1$-$C_{20}$ alkyl group, said $C_2$-$C_{20}$ alkenyl group, said $C_6$-$C_{10}$ aryl group and said adamantyl group may be optionally substituted with up to three groups, each independently selected from halo, —O$R^{16}$, —C(O)O$R^{16}$, CN, $NO_2$, $C_1$-$C_6$ haloalkyl, $C_1$-$C_6$ hydroxyalkyl, $C_3$-$C_7$ cycloalkyl, $C_6$-$C_{10}$ aryl, 5- or 6-membered monocyclic heteroaryl, 9- or 10-membered bicyclic heteroaryl, —N($R^{16}$)$_2$, —C(O)N($R^{16}$)$_2$, —S$R^{16}$, —S(O)$R^{16}$, —S(O)$_2$R$^{16}$, —S(O)$_2$N(R$^{16}$)$_2$, —NHC(O)R$^{16}$, —NHC(O)OR$^{16}$ and —NHC(O)N(R$^{16}$)$_2$;

R$^{15}$ is H, C$_6$-C$_{10}$ aryl, 5- or 6-membered monocyclic heteroaryl or 9- or 10-membered bicyclic heteroaryl, wherein said C$_6$-C$_{10}$ aryl group, said 5- or 6-membered monocyclic heteroaryl group and said 9- or 10-membered bicyclic heteroaryl group may be optionally substituted with R$^{17}$;

each occurrence of R$^{16}$ is independently H, C$_1$-C$_{10}$ alkyl, C$_1$-C$_6$ haloalkyl, C$_1$-C$_6$ hydroxyalkyl, —(C$_1$-C$_3$ alkylene)$_m$-(C$_3$-C$_7$ cycloalkyl), —(C$_1$-C$_3$ alkylene)$_m$-(C$_6$-C$_{10}$ aryl), —(C$_1$-C$_3$ alkylene)$_m$-(4 to 7-membered heterocycloalkyl), —(C$_1$-C$_3$ alkylene)$_m$-(5- or 6-membered monocyclic heteroaryl) or —(C$_1$-C$_3$ alkylene)$_m$-(9- or 10-membered bicyclic heteroaryl), wherein said C$_3$-C$_7$ cycloalkyl group, said C$_6$-C$_{10}$ aryl group, said 4 to 7-membered heterocycloalkyl group, said -5- or 6-membered monocyclic heteroaryl group or said 9- or 10-membered bicyclic heteroaryl group may be optionally substituted with R$^{17}$;

R$^{17}$ represents from one to five substituent groups, each independently selected from C$_1$-C$_6$ alkyl, halo, —OR$^{19}$, —SR$^{19}$, C$_1$-C$_6$ haloalkyl, C$_1$-C$_6$ hydroxyalkyl, —O—(C$_1$-C$_6$ haloalkyl), —CN, —NO$_2$, —N(R$^{19}$)$_2$, —C(O)OR$^{19}$, —C(O)N(R$^{19}$)$_2$ and —NHC(O)R$^{19}$;

each occurence of R$^{18}$ is independently selected from H, C$_1$-C$_6$ alkyl, C$_6$-C$_{10}$ aryl, —(C$_1$-C$_6$ alkylene)-O—(C$_1$-C$_{20}$ alkyl), —(C$_1$-C$_6$ alkylene)-O—C(O)—R$^{16}$, and —(C$_1$-C$_6$ alkylene)-O—C(O)—O—R$^{16}$;

each occurrence of R$^{19}$ is independently H, C$_1$-C$_{10}$ alkyl, C$_1$-C$_6$ haloalkyl, C$_1$-C$_6$ hydroxyalkyl, —(C$_1$-C$_3$ alkylene)$_m$-(C$_3$-C$_7$ cycloalkyl), —(C$_1$-C$_3$ alkylene)$_m$-(C$_6$-C$_{10}$ aryl), —(C$_1$-C$_3$ alkylene)$_m$-(4 to 7-membered heterocycloalkyl), —(C$_1$-C$_3$ alkylene)$_m$-(5- or 6-membered monocyclic heteroaryl) or —(C$_1$-C$_3$ alkylene)$_m$-(9- or 10-membered bicyclic heteroaryl);

each occurence of R$^{20}$ is independently selected from H, C$_1$-C$_6$ alkyl and —(C$_1$-C$_6$ alkylene)$_m$-Z—(C$_1$-C$_3$ alkylene)$_m$-R$^{11}$;

each occurrence of Z is independently selected from a bond, —O— or —N(R$^9$)—;

each occurrence of m is independently 0 or 1; and each occurrence of p is independently 0 or 1, such that at least one occurrence of R$^{11}$ must be present in the compound of formula (I).

The Compounds of Formula (I) (also referred to herein as the "Amido-Substituted Pyridotriazine Derivatives") and pharmaceutically acceptable salts thereof may be useful, for example, for inhibiting HIV viral replication or replicon activity, and for treating or preventing HIV infection in a subject. Without being bound by any specific theory, it is believed that the Amido-Substituted Pyridotriazine Derivatives inhibit HIV viral replication by inhibiting HIV Integrase.

Accordingly, the present invention provides methods for treating or preventing HIV infection in a subject, comprising administering to the subject an effective amount of at least one Amido-Substituted Pyridotriazine Derivative.

The details of the invention are set forth in the accompanying detailed description below.

Although any methods and materials similar to those described herein may be used in the practice or testing of the present invention, illustrative methods and materials are now described. Other embodiments, aspects and features of the present invention are either further described in or will be apparent from the ensuing description, examples and appended claims.

DETAILED DESCRIPTION OF THE INVENTION

The present invention includes Amido-Substituted Pyridotriazine Derivatives, compositions comprising at least one Amido-Substituted Pyridotriazine Derivative, and methods of using the Amido-Substituted Pyridotriazine Derivatives for treating or preventing HIV infection in a subject.

Definitions and Abbreviations

The terms used herein have their ordinary meaning and the meaning of such terms is independent at each occurrence thereof. That notwithstanding and except where stated otherwise, the following definitions apply throughout the specification and claims. Chemical names, common names, and chemical structures may be used interchangeably to describe the same structure. These definitions apply regardless of whether a term is used by itself or in combination with other terms, unless otherwise indicated. Hence, the definition of "alkyl" applies to "alkyl" as well as the "alkyl" portions of "hydroxyalkyl," "haloalkyl," "—O-alkyl," etc. . . .

As used herein, and throughout this disclosure, the following terms, unless otherwise indicated, shall be understood to have the following meanings:

A "subject" is a human or non-human mammal. In one embodiment, a subject is a human. In another embodiment, a subject is a primate. In another embodiment, a subject is a monkey. In another embodiment, a subject is a chimpanzee. In still another embodiment, a subject is a rhesus monkey.

The term "effective amount" as used herein, refers to an amount of Amido-Substituted Pyridotriazine Derivative and/or an additional therapeutic agent, or a composition thereof that is effective in producing the desired therapeutic, ameliorative, inhibitory or preventative effect when administered to a subject suffering from HIV infection or AIDS. In the combination therapies of the present invention, an effective amount can refer to each individual agent or to the combination as a whole, wherein the amounts of all agents administered are together effective, but wherein the component agent of the combination may not be present individually in an effective amount.

The term "preventing," as used herein with respect to an HIV viral infection or AIDS, refers to reducing the likelihood or severity of HIV infection or AIDS.

The term "alkyl," as used herein, refers to an aliphatic hydrocarbon group having one of its hydrogen atoms replaced with a bond. An alkyl group may be straight or branched and contain from about 1 to about 20 carbon atoms. In one embodiment, an alkyl group contains from about 1 to about 12 carbon atoms. In different embodiments, an alkyl group contains from 1 to 6 carbon atoms (C$_1$-C$_6$ alkyl) or from about 1 to about 4 carbon atoms (C$_1$-C$_4$ alkyl). Non-limiting examples of alkyl groups include methyl, ethyl, n-propyl, isopropyl, n-butyl, sec-butyl, isobutyl, tert-butyl, n-pentyl, neopentyl, isopentyl, n-hexyl, isohexyl and neohexyl. An alkyl group may be unsubstituted or substituted by one or more substituents which may be the same or different. Illustrative examples of substituents include, but are not limited to, halo, alkenyl, alkynyl, aryl, cycloalkyl, cyano, hydroxy, —O-alkyl, —O-aryl, -alkylene-O-alkyl, alkylthio, —NH$_2$, —NH(alkyl), —N(alkyl)$_2$, —NH(cycloalkyl), —O—C(O)-alkyl, —O—C(O)-aryl, —O—C(O)-cycloalkyl, —C(O)OH and —C(O)O-alkyl. In one embodiment, an alkyl group is linear. In another embodiment, an alkyl group is branched. Unless otherwise indicated, an alkyl group is unsubstituted.

The term "alkenyl," as used herein, refers to an aliphatic hydrocarbon group containing at least one carbon-carbon double bond and having one of its hydrogen atoms replaced with a bond. An alkenyl group may be straight or branched and contain from about 2 to about 15 carbon atoms. In one embodiment, an alkenyl group contains from about 2 to about 12 carbon atoms. In another embodiment, an alkenyl group contains from about 2 to about 6 carbon atoms. Non-limiting examples of alkenyl groups include ethenyl, propenyl, n-butenyl, 3-methylbut-2-enyl, n-pentenyl, octenyl and decenyl. An alkenyl group may be unsubstituted or substituted by one or more substituents which may be the same or different. Illustrative examples of substituents include, but are not limited to, halo, alkenyl, alkynyl, aryl, cycloalkyl, cyano, hydroxy, —O-alkyl, —O-aryl, -alkylene-O-alkyl, alkylthio, —NH$_2$, —NH(alkyl), —N(alkyl)$_2$, —NH(cycloalkyl), —O—C(O)-alkyl, —O—C(O)-aryl, —O—C(O)-cycloalkyl, —C(O)OH and —C(O)O-alkyl. The term "C$_2$-C$_6$ alkenyl" refers to an alkenyl group having from 2 to 6 carbon atoms. Unless otherwise indicated, an alkenyl group is unsubstituted.

The term "alkynyl," as used herein, refers to an aliphatic hydrocarbon group containing at least one carbon-carbon triple bond and having one of its hydrogen atoms replaced with a bond. An alkynyl group may be straight or branched and contain from about 2 to about 15 carbon atoms. In one embodiment, an alkynyl group contains from about 2 to about 12 carbon atoms. In another embodiment, an alkynyl group contains from about 2 to about 6 carbon atoms. Non-limiting examples of alkynyl groups include ethynyl, propynyl, 2-butynyl and 3-methylbutynyl. An alkynyl group may be unsubstituted or substituted by one or more substituents which may be the same or different. Illustrative examples of substituents include, but are not limited to, halo, alkenyl, alkynyl, aryl, cycloalkyl, cyano, hydroxy, —O-alkyl, —O-aryl, -alkylene-O-alkyl, alkylthio, —NH$_2$, —NH(alkyl), —N(alkyl)$_2$, —NH(cycloalkyl), —O—C(O)-alkyl, —O—C(O)-aryl, —O—C(O)-cycloalkyl, —C(O)OH and —C(O)O-alkyl. The term "C$_2$-C$_6$ alkynyl" refers to an alkynyl group having from 2 to 6 carbon atoms. Unless otherwise indicated, an alkynyl group is unsubstituted.

The term "alkylene," as used herein, refers to an alkyl group, as defined above, wherein one of the alkyl group's hydrogen atoms has been replaced with a bond. Non-limiting examples of alkylene groups include —CH$_2$—, —CH$_2$CH$_2$—, —CH$_2$CH$_2$CH$_2$—, —CH$_2$CH$_2$CH$_2$CH$_2$—, —CH(CH$_3$)CH$_2$CH$_2$—, —CH(CH$_3$)— and —CH$_2$CH(CH$_3$)CH$_2$—. In one embodiment, an alkylene group has from 1 to about 6 carbon atoms. In another embodiment, an alkylene group has from about 3 to about 5 carbon atoms. In another embodiment, an alkylene group is branched. In another embodiment, an alkylene group is linear. In one embodiment, an alkylene group is —CH$_2$—. The term "C$_1$-C$_6$ alkylene" refers to an alkylene group having from 1 to 6 carbon atoms. The term "C$_1$-C$_3$ alkylene" refers to an alkylene group having from 1 to 3 carbon atoms.

The term "alkenylene," as used herein, refers to an alkenyl group, as defined above, wherein one of the alkenyl group's hydrogen atoms has been replaced with a bond. Non-limiting examples of alkenylene groups include —CH═CH—, —CH═CHCH$_2$—, —CH$_2$CH═CH—, —CH$_2$CH═CHCH$_2$—, —CH═CHCH$_2$CH$_2$—, —CH$_2$CH$_2$CH═CH— and —CH(CH$_3$)CH═CH—. In one embodiment, an alkenylene group has from 2 to about 6 carbon atoms. In another embodiment, an alkenylene group has from about 2 to about 4 carbon atoms. In another embodiment, an alkenylene group is branched. In another embodiment, an alkenylene group is linear. The term "C$_2$-C$_6$ alkylene" refers to an alkenylene group having from 2 to 6 carbon atoms. The term "C$_2$-C$_4$ alkenylene" refers to an alkylene group having from 2 to 4 carbon atoms.

The term "aryl," as used herein, refers to an aromatic monocyclic or multicyclic ring system comprising from about 6 to about 14 carbon atoms. In one embodiment, an aryl group contains from about 6 to about 10 carbon atoms. An aryl group may be optionally substituted with one or more "ring system substituents" which may be the same or different, and are as defined herein below. In one embodiment, an aryl group may be optionally fused to a cycloalkyl or cycloalkanoyl group. Non-limiting examples of aryl groups include phenyl and naphthyl. In one embodiment, an aryl group is phenyl. Unless otherwise indicated, an aryl group is unsubstituted.

The term "arylene," as used herein, refers to a bivalent group derived from an aryl group, as defined above, by removal of a hydrogen atom from a ring carbon of an aryl group. An arylene group may be derived from a monocyclic or multicyclic ring system comprising from about 6 to about 14 carbon atoms. In one embodiment, an arylene group contains from about 6 to about 10 carbon atoms. In another embodiment, an arylene group is a naphthylene group. In another embodiment, an arylene group is a phenylene group. An arylene group may be optionally substituted with one or more "ring system substituents" which may be the same or different, and are as defined herein below. An arylene group is divalent and either available bond on an arylene group can connect to either group flanking the arylene group. For example, the group "A-arylene-B," wherein the arylene group is:

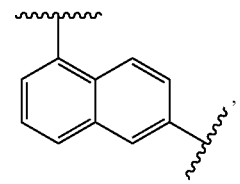 [SMILES: *c1ccc2c(*)cccc2c1]

is understood to represent both:

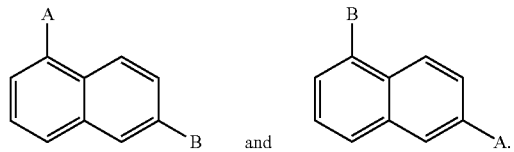

In one embodiment, an arylene group may be optionally fused to a cycloalkyl or cycloalkanoyl group. Non-limiting examples of arylene groups include phenylene and naphthalene. In one embodiment, an arylene group is unsubstituted. In another embodiment, an arylene group is:

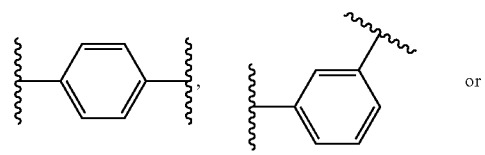

or

-continued

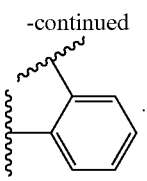

Unless otherwise indicated, an arylene group is unsubstituted.

The term "cycloalkyl," as used herein, refers to a saturated or unsaturated, non-aromatic mono- or multicyclic ring system comprising from about 3 to about 10 ring carbon atoms. In one embodiment, a cycloalkyl contains from about 5 to about 10 ring carbon atoms. In another embodiment, a cycloalkyl contains from about 3 to about 7 ring atoms. In another embodiment, a cycloalkyl contains from about 5 to about 6 ring atoms. The term "cycloalkyl" also encompasses a cycloalkyl group, as defined above, which is fused to an aryl (e.g., benzene) or heteroaryl ring, such as tetrahydronaphthalene and the like. Non-limiting examples of monocyclic cycloalkyls include cyclopropyl, cyclobutyl, cyclopentyl, cyclohexyl, cycloheptyl and cyclooctyl. Non-limiting examples of multicyclic cycloalkyls include 1-decalinyl, norbornyl and adamantyl. A cycloalkyl group may be optionally substituted with one or more "ring system substituents" which may be the same or different, and are as defined herein below. In one embodiment, a cycloalkyl group is unsubstituted. The term "3 to 7-membered cycloalkyl" refers to a cycloalkyl group having from 3 to 7 ring carbon atoms. Unless otherwise indicated, a cycloalkyl group is unsubstituted. A ring carbon atom of a cycloalkyl group may be functionalized as a carbonyl group. An illustrative example of such a cycloalkyl group (also referred to herein as a "cycloalkanoyl" group) includes, but is not limited to, cyclobutanoyl:

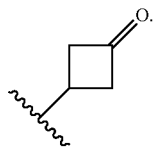 [SMILES: *C1CC(=O)C1]

The term "halo," as used herein, means F, —Cl, —Br or —I.

The term "haloalkyl," as used herein, refers to an alkyl group as defined above, wherein one or more of the alkyl group's hydrogen atoms has been replaced with a halogen. In one embodiment, a haloalkyl group has from 1 to 6 carbon atoms. In another embodiment, a haloalkyl group is substituted with from 1 to 3 F atoms. Non-limiting examples of haloalkyl groups include —$CH_2F$, —$CHF_2$, —$CF_3$, —$CH_2Cl$ and —$CCl_3$. The term "$C_1$-$C_6$ haloalkyl" refers to a haloalkyl group having from 1 to 6 carbon atoms.

The term "hydroxyalkyl," as used herein, refers to an alkyl group as defined above, wherein one or more of the alkyl group's hydrogen atoms have been replaced with an OH group. In one embodiment, a hydroxyalkyl group has from 1 to 6 carbon atoms. Non-limiting examples of hydroxyalkyl groups include —$CH_2OH$, —$CH_2CH_2OH$, —$CH_2CH_2CH_2OH$ and —$CH_2CH(OH)CH_3$. The term "$C_1$-$C_6$ hydroxyalkyl" refers to a hydroxyalkyl group having from 1 to 6 carbon atoms.

The term "heteroaryl," as used herein, refers to an aromatic monocyclic or multicyclic ring system comprising about 5 to about 14 ring atoms, wherein from 1 to 4 of the ring atoms is independently O, N or S and the remaining ring atoms are carbon atoms. In one embodiment, a heteroaryl group has 5 to 10 ring atoms. In another embodiment, a heteroaryl group is monocyclic and has 5 or 6 ring atoms. In another embodiment, a heteroaryl group is bicyclic. A heteroaryl group may be optionally substituted by one or more "ring system substituents" which may be the same or different, and are as defined herein below. A heteroaryl group is joined via a ring carbon atom, and any nitrogen atom of a heteroaryl may be optionally oxidized to the corresponding N-oxide. The term "heteroaryl" also encompasses a heteroaryl group, as defined above, which is fused to a benzene ring. Non-limiting examples of heteroaryls include pyridyl, pyrazinyl, furanyl, thienyl, pyrimidinyl, pyridone (including N-substituted pyridones), isoxazolyl, isothiazolyl, oxazolyl, oxadiazolyl, thiazolyl, pyrazolyl, furazanyl, pyrrolyl, triazolyl, 1,3,4-thiadiazolyl, pyrazinyl, pyridazinyl, quinoxalinyl, phthalazinyl, oxindolyl, imidazo[1,2-a]pyridinyl, imidazo[2,1-b]thiazolyl, benzofurazanyl, indolyl, azaindolyl, benzimidazolyl, benzothienyl, quinolinyl, imidazolyl, benzimidazolyl, thienopyridyl, quinazolinyl, thienopyrimidyl, pyrrolopyridyl, imidazopyridyl, isoquinolinyl, benzoazaindolyl, 1,2,4-triazinyl, benzothiazolyl and the like, and all isomeric forms thereof. The term "heteroaryl" also refers to partially saturated heteroaryl moieties such as, for example, tetrahydroisoquinolyl, tetrahydroquinolyl and the like. In one embodiment, a heteroaryl group is a 5-membered heteroaryl. In another embodiment, a heteroaryl group is a 6-membered monocyclic heteroaryl. In another embodiment, a heteroaryl group comprises a 5- to 6-membered monocyclic heteroaryl group fused to a benzene ring. Unless otherwise indicated, a heteroaryl group is unsubstituted.

The term "heterocycloalkyl," as used herein, refers to a non-aromatic saturated or unsaturated, monocyclic or multicyclic ring system comprising 3 to about 11 ring atoms, wherein from 1 to 4 of the ring atoms are independently O, S, N or Si, and the remainder of the ring atoms are carbon atoms. A heterocycloalkyl group may be joined via a ring carbon, ring silicon atom or ring nitrogen atom. In one embodiment, a heterocycloalkyl group is monocyclic and has from about 3 to about 7 ring atoms. In another embodiment, a heterocycloalkyl group is monocyclic has from about 4 to about 7 ring atoms. In another embodiment, a heterocycloalkyl group is bicyclic and has from about 7 to about 11 ring atoms. In still another embodiment, a heterocycloalkyl group is monocyclic and has 5 or 6 ring atoms. In one embodiment, a heterocycloalkyl group is monocyclic. In another embodiment, a heterocycloalkyl group is bicyclic. There are no adjacent oxygen and/or sulfur atoms present in the ring system. Any —NH group in a heterocycloalkyl ring may exist protected such as, for example, as an —N(BOC), —N(Cbz), —N(Tos) group and the like; such protected heterocycloalkyl groups are considered part of this invention. The term "heterocycloalkyl" also encompasses a heterocycloalkyl group, as defined above, which is fused to an aryl (e.g., benzene) or heteroaryl ring, such as dihydrobenzofuran and the like. A heterocycloalkyl group may be optionally substituted by one or more "ring system substituents" which may be the same or different, and are as defined herein below. The nitrogen or sulfur atom of the heterocycloalkyl may be optionally oxidized to the corresponding N-oxide, S-oxide or S,S-dioxide. Non-limiting examples of monocyclic heterocycloalkyl rings include oxetanyl, piperidyl, pyrrolidinyl, piperazinyl, morpholinyl, thiomorpholinyl, thiazolidinyl, 1,4-dioxanyl, tetrahydrofuranyl, pyranyl, tetrahydrothiophenyl, delta-lactam, delta-lactone and the like, and all isomers thereof.

A ring carbon atom of a heterocycloalkyl group may be functionalized as a carbonyl group. An illustrative example of such a heterocycloalkyl group is:

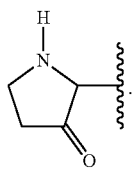 [SMILES: *C1NCCC1=O]

In one embodiment, a heterocycloalkyl group is a 5-membered monocyclic heterocycloalkyl. In another embodiment, a heterocycloalkyl group is a 6-membered monocyclic heterocycloalkyl. The term "3 to 6-membered monocyclic heterocycloalkyl" refers to a monocyclic heterocycloalkyl group having from 3 to 6 ring atoms. The term "4 to 7-membered monocyclic heterocycloalkyl" refers to a monocyclic heterocycloalkyl group having from 4 to 7 ring atoms. The term "7 to 11-membered bicyclic heterocycloalkyl" refers to a bicyclic heterocycloalkyl group having from 7 to 11 ring atoms. Unless otherwise indicated, a heterocycloalkyl group is unsubstituted.

The term "ring system substituent," as used herein, refers to a substituent group attached to an aromatic or non-aromatic ring system which, for example, replaces an available hydrogen on the ring system. Ring system substituents may be the same or different. Illustrative examples of ring system substituents include, but are not limited to, alkyl, alkenyl, alkynyl, aryl, heteroaryl, -alkylene-aryl, -arylene-alkyl, -alkylene-heteroaryl, -alkenylene-heteroaryl, -alkynylene-heteroaryl, —OH, hydroxyalkyl, haloalkyl, —O-alkyl, —O-haloalkyl, -alkylene-O-alkyl, —O-aryl, —O-alkylene-aryl, acyl, —C(O)-aryl, halo, —NO$_2$, —CN, —SF$_5$, —C(O)OH, —C(O)O-alkyl, —C(O)O-aryl, —C(O)O-alkylene-aryl, —S(O)-alkyl, —S(O)$_2$-alkyl, —S(O)-aryl, —S(O)$_2$-aryl, —S(O)-heteroaryl, —S(O)$_2$-heteroaryl, —S-alkyl, —S-aryl, —S-heteroaryl, —S-alkylene-aryl, —S-alkylene-heteroaryl, —S(O)$_2$-alkylene-aryl, —S(O)$_2$-alkylene-heteroaryl, —Si(alkyl)$_2$, —Si(aryl)$_2$, —Si(heteroaryl)$_2$, —Si(alkyl)(aryl), —Si(alkyl)(cycloalkyl), —Si(alkyl)(heteroaryl), cycloalkyl, heterocycloalkyl, —O—C(O)-alkyl, —O—C(O)-aryl, —O—C(O)-cycloalkyl, —C(=N—CN)—NH$_2$, —C(=NH)—NH$_2$, —C(=NH)—NH(alkyl), —N(Y$_1$)(Y$_2$), -alkylene-N(Y$_1$)(Y$_2$), —C(O)N(Y$_1$)(Y$_2$) and —S(O)$_2$N(Y$_1$)(Y$_2$), wherein Y$_1$ and Y$_2$ may be the same or different and are independently selected from the group consisting of hydrogen, alkyl, aryl, cycloalkyl, and alkylene-aryl. "Ring system substituent" may also mean a single moiety which simultaneously replaces two available hydrogens on two adjacent carbon atoms (one H on each carbon) on a ring system. Examples of such moiety are methylenedioxy, ethylenedioxy, —C(CH$_3$)$_2$— and the like which form moieties such as, for example:

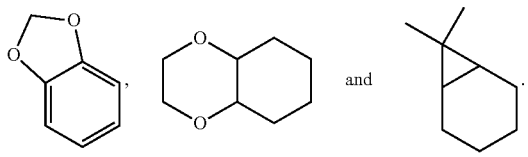

The term "substituted" means that one or more hydrogens on the designated atom is replaced with a selection from the indicated group, provided that the designated atom's normal valency under the existing circumstances is not exceeded, and that the substitution results in a stable compound. Combinations of substituents and/or variables are permissible only if such combinations result in stable compounds. By "stable compound' or "stable structure" is meant a compound that is sufficiently robust to survive isolation to a useful degree of purity from a reaction mixture, and formulation into an efficacious therapeutic agent.

The term "in substantially purified form," as used herein, refers to the physical state of a compound after the compound is isolated from a synthetic process (e.g., from a reaction mixture), a natural source, or a combination thereof. The term "in substantially purified form," also refers to the physical state of a compound after the compound is obtained from a purification process or processes described herein or well-known to the skilled artisan (e.g., chromatography, recrystallization and the like), in sufficient purity to be characterizable by standard analytical techniques described herein or well-known to the skilled artisan.

It should also be noted that any carbon as well as heteroatom with unsatisfied valences in the text, schemes, examples and tables herein is assumed to have the sufficient number of hydrogen atom(s) to satisfy the valences.

When a functional group in a compound is termed "protected", this means that the group is in modified form to preclude undesired side reactions at the protected site when the compound is subjected to a reaction. Suitable protecting groups will be recognized by those with ordinary skill in the art as well as by reference to standard textbooks such as, for example, T. W. Greene et al, *Protective Groups in Organic Synthesis* (1991), Wiley, New York.

When any substituent or variable (e.g., alkyl, R$^1$, R$^7$, etc.) occurs more than one time in any constituent or in Formula (I), its definition on each occurrence is independent of its definition at every other occurrence, unless otherwise indicated.

As used herein, the term "composition" is intended to encompass a product comprising the specified ingredients in the specified amounts, as well as any product which results, directly or indirectly, from combination of the specified ingredients in the specified amounts.

Prodrugs and solvates of the compounds of the invention are also contemplated herein. A discussion of prodrugs is provided in T. Higuchi and V. Stella, *Pro-drugs as Novel Delivery Systems* (1987) 14 of the A.C.S. Symposium Series, and in *Bioreversible Carriers in Drug Design*, (1987) Edward B. Roche, ed., American Pharmaceutical Association and Pergamon Press. The term "prodrug" means a compound (e.g., a drug precursor) that is transformed in vivo to provide an Amido-Substituted Pyridotriazine Derivative or a pharmaceutically acceptable salt of the compound. The transformation may occur by various mechanisms (e.g., by metabolic or chemical processes), such as, for example, through hydrolysis in blood. For example, if an Amido-Substituted Pyridotriazine Derivative or a pharmaceutically acceptable salt, hydrate or solvate of the compound contains a carboxylic acid functional group, a prodrug can comprise an ester formed by the replacement of the hydrogen atom of the acid group with a group such as, for example, (C$_1$-C$_8$) alkyl, (C$_2$-C$_{12}$)alkanoyloxymethyl, 1-(alkanoyloxy)ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl- 1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino)ethyl having from 4 to 10 carbon atoms, 3-phthalidyl, 4-crotonolactonyl, gamma-butyrolacton-4-yl, di-N,N—($C_1$-$C_2$)alkylamino($C_2$-$C_3$)alkyl (such as (3-dimethylaminoethyl), carbamoyl-($C_1$-$C_2$)alkyl, N,N-di ($C_1$-$C_2$)alkylcarbamoyl-($C_1$-$C_2$)alkyl and piperidino-, pyrrolidino- or morpholino($C_2$-$C_3$)alkyl, and the like.

Similarly, if an Amido-Substituted Pyridotriazine Derivative contains an alcohol functional group, a prodrug may be formed by the replacement of one or more of the hydrogen atoms of the alcohol groups with a group such as, for example, ($C_1$-$C_6$)alkanoyloxymethyl, 1-(($C^1$-$C_6$)alkanoyloxy)ethyl, 1-methyl-1-(($C_1$-$C_6$)alkanoyloxy)ethyl, ($C_1$-$C_6$) alkoxycarbonyloxymethyl, N—($C_1$-$C_6$)alkoxycarbonylaminomethyl, succinoyl, ($C_1$-$C_6$)alkanoyl, α-amino($C_1$-$C_4$) alkyl, α-amino($C_1$-$C_4$)alkylene-aryl, arylacyl and α-aminoacyl, or α-aminoacyl-α-aminoacyl, where each α-aminoacyl group is independently selected from the naturally occurring L-amino acids, or glycosyl (the radical resulting from the removal of a hydroxyl group of the hemiacetal form of a carbohydrate).

If an Amido-Substituted Pyridotriazine Derivative incorporates an amine functional group, a prodrug may be formed by the replacement of a hydrogen atom in the amine group with a group such as, for example, R-carbonyl-, RO-carbonyl-, NRR'-carbonyl- wherein R and R' are each independently ($C_1$-$C_{10}$)alkyl, ($C_3$-$C_7$) cycloalkyl, benzyl, a natural α-aminoacyl, —C(OH)C(O)O$Y^1$ wherein $Y^1$ is H, ($C_1$-$C_6$) alkyl or benzyl, —C(O$Y^2$)$Y^3$ wherein $Y^2$ is ($C_1$-$C_4$) alkyl and $Y^3$ is ($C_1$-$C_6$)alkyl; carboxy ($C_1$-$C_6$)alkyl; amino($C_1$-$C_4$)alkyl or mono-N- or di-N,N—($C_1$-$C_6$)alkylaminoalkyl; —C($Y^4$)$Y^5$ wherein $Y^4$ is H or methyl and $Y^5$ is mono-N— or di-N,N—($C_1$-$C_6$)alkylamino morpholino; piperidin-1-yl or pyrrolidin-1-yl, and the like.

Pharmaceutically acceptable esters of the present compounds include the following groups: (1) carboxylic acid esters obtained by esterification of the hydroxy group of a hydroxyl compound, in which the non-carbonyl moiety of the carboxylic acid portion of the ester grouping is selected from straight or branched chain alkyl (e.g., methyl, ethyl, n-propyl, isopropyl, t-butyl, sec-butyl or n-butyl), alkoxyalkyl (e.g., methoxymethyl), aralkyl (e.g., benzyl), aryloxyalkyl (for example, phenoxymethyl), aryl (e.g., phenyl optionally substituted with, for example, halogen, $C_{1-4}$alkyl, —O—($C_{1-4}$)alkyl) or amino); (2) sulfonate esters, such as alkyl- or aralkylsulfonyl (for example, methanesulfonyl); (3) amino acid esters, including those corresponding to both natural and non-natural amino acids (e.g., L-valyl or L-isoleucyl); (4) phosphonate esters and (5) mono-, di- or triphosphate esters. The phosphate esters may be further esterified by, for example, a $C_{1-20}$ alcohol or reactive derivative thereof, or by a 2,3-di ($C_{6-24}$)acyl glycerol.

One or more compounds of the invention may exist in unsolvated as well as solvated forms with pharmaceutically acceptable solvents such as water, ethanol, and the like, and it is intended that the invention embrace both solvated and unsolvated forms. "Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of solvates include ethanolates, methanolates, and the like. A "hydrate" is a solvate wherein the solvent molecule is water.

One or more compounds of the invention may optionally be converted to a solvate. Preparation of solvates is generally known. Thus, for example, M. Caira et al, *J. Pharmaceutical Sci.*, 93(3), 601-611 (2004) describe the preparation of the solvates of the antifungal fluconazole in ethyl acetate as well as from water. Similar preparations of solvates, hemisolvate, hydrates and the like are described by E. C. van Tonder et al, *AAPS PharmSciTechours*, 5(1), article 12 (2004); and A. L. Bingham et al, *Chem. Commun.*, 603-604 (2001). A typical, non-limiting, process involves dissolving the inventive compound in desired amounts of the desired solvent (organic or water or mixtures thereof) at a higher than room temperature, and cooling the solution at a rate sufficient to form crystals which are then isolated by standard methods. Analytical techniques such as, for example IR spectroscopy, show the presence of the solvent (or water) in the crystals as a solvate (or hydrate).

The Amido-Substituted Pyridotriazine Derivatives can form salts which are also within the scope of this invention. Reference to an Amido-Substituted Pyridotriazine Derivative herein is understood to include reference to salts thereof, unless otherwise indicated. The term "salt(s)", as employed herein, denotes acidic salts formed with inorganic and/or organic acids, as well as basic salts formed with inorganic and/or organic bases. In addition, when an Amido-Substituted Pyridotriazine Derivative contains both a basic moiety, such as, but not limited to a pyridine or imidazole, and an acidic moiety, such as, but not limited to a carboxylic acid, zwitterions ("inner salts") may be formed and are included within the term "salt(s)" as used herein. In one embodiment, the salt is a pharmaceutically acceptable (i.e., non-toxic, physiologically acceptable) salt. In another embodiment, the salt is other than a pharmaceutically acceptable salt. Salts of the Compounds of Formula (I) may be formed, for example, by reacting an Amido-Substituted Pyridotriazine Derivative with an amount of acid or base, such as an equivalent amount, in a medium such as one in which the salt precipitates or in an aqueous medium followed by lyophilization.

Exemplary acid addition salts include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates, naphthalenesulfonates, nitrates, oxalates, phosphates, propionates, salicylates, succinates, sulfates, tartarates, thiocyanates, toluenesulfonates (also known as tosylates) and the like. Additionally, acids which are generally considered suitable for the formation of pharmaceutically useful salts from basic pharmaceutical compounds are discussed, for example, by P. Stahl et al, Camille G. (eds.) *Handbook of Pharmaceutical Salts*. Properties, Selection and Use. (2002) Zurich: Wiley-VCH; S. Berge et al, *Journal of Pharmaceutical Sciences* (1977) 66(1) 1-19; P. Gould, *International J. of Pharmaceutics* (1986) 33 201-217; Anderson et al, *The Practice of Medicinal Chemistry* (1996), Academic Press, New York; and in *The Orange Book* (Food & Drug Administration, Washington, D.C. on their website). These disclosures are incorporated herein by reference thereto.

Exemplary basic salts include ammonium salts, alkali metal salts such as sodium, lithium, and potassium salts, alkaline earth metal salts such as calcium and magnesium salts, salts with organic bases (for example, organic amines) such as dicyclohexylamine, t-butyl amine, choline, and salts with amino acids such as arginine, lysine and the like. Basic nitrogen-containing groups may be quarternized with agents such as lower alkyl halides (e.g., methyl, ethyl, and butyl chlorides, bromides and iodides), dialkyl sulfates (e.g., dimethyl, diethyl, and dibutyl sulfates), long chain halides (e.g., decyl, lauryl, and stearyl chlorides, bromides and iodides), aralkyl halides (e.g., benzyl and phenethyl bromides), and others.

All such acid salts and base salts are intended to be pharmaceutically acceptable salts within the scope of the invention and all acid and base salts are considered equivalent to the free forms of the corresponding compounds for purposes of the invention.

Diastereomeric mixtures may be separated into their individual diastereomers on the basis of their physical chemical differences by methods well-known to those skilled in the art, such as, for example, by chromatography and/or fractional crystallization. Enantiomers may be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Stereochemically pure compounds may also be prepared by using chiral starting materials or by employing salt resolution techniques. Also, some of the Amido-Substituted Pyridotriazine Derivatives may be atropisomers (e.g., substituted biaryls) and are considered as part of this invention. Enantiomers can also be directly separated using chiral chromatographic techniques.

It is also possible that the Amido-Substituted Pyridotriazine Derivatives may exist in different tautomeric forms, and all such forms are embraced within the scope of the invention. For example, all keto-enol and imine-enamine forms of the compounds are included in the invention.

All stereoisomers (for example, geometric isomers, optical isomers and the like) of the present compounds (including those of the salts, solvates, hydrates, esters and prodrugs of the compounds as well as the salts, solvates and esters of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention. If an Amido-Substituted Pyridotriazine Derivative incorporates a double bond or a fused ring, both the cis- and trans-forms, as well as mixtures, are embraced within the scope of the invention.

Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the *IUPAC* 1974 Recommendations. The use of the terms "salt", "solvate", "ester", "prodrug" and the like, is intended to apply equally to the salt, solvate, ester and prodrug of enantiomers, stereoisomers, rotamers, tautomers, racemates or prodrugs of the inventive compounds.

In the Compounds of Formula (I), the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of generic Formula I. For example, different isotopic forms of hydrogen (H) include protium ($^1$H) and deuterium ($^2$H). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched Compounds of Formula (I) may be prepared without undue experimentation by conventional techniques well known to those skilled in the art or by processes analogous to those described in the Schemes and Examples herein using appropriate isotopically-enriched reagents and/or intermediates. In one embodiment, a Compound of Formula (I) has one or more of its hydrogen atoms replaced with deuterium.

Polymorphic forms of the Amido-Substituted Pyridotriazine Derivatives, and of the salts, solvates, hydrates, esters and prodrugs of the Amido-Substituted Pyridotriazine Derivatives, are intended to be included in the present invention.

List of Abbreviations

Anal.=analytical
Bn=benzyl
DCM=dichloromethane
DMF=dimethylformamide
DMSO=dimethylsulfoxide
EDC=1-ethyl-3-(3-dimethylaminopropyl)carbodiimide
Ent A=enantiomer A
Ent B=enantiomer B
EtOAc=ethyl acetate
EtOH=ethanol
HOBT=1-hydroxy-1H-benzotriazole
HPLC=high-pressure liquid chromatography
LCMS=liquid chromatography-mass spectrometry
Me=methyl
MeOH'=methanol
MS=mass spectroscopy
NHS=normal human serum
NMR=nuclear magnetic resonance spectroscopy
Pd/C=palladium on carbon
Pd(Ph$_3$P)$_4$=tetrakis triphenylphosphine palladium(0)
RP-MPLC=reverse-phase medium pressure liquid chromatography
Rt or RT=room temperature
TFA=trifluoroacetic acid
THF=tetrahydrofuran
TLC=thin-layer chromatography
TMS-Br=trimethylsilyl bromide The Compounds of Formula (I)

The present invention provides Spirocyclic Pyridotriazine Derivatives of Formula (I):

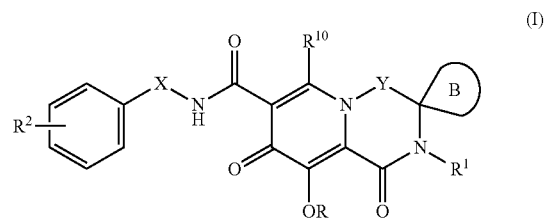

and pharmaceutically acceptable salts thereof, wherein B, X, Y, R, R$^1$, R$^2$ and R$^{10}$ are defined above for the Compounds of Formula (I).

In one embodiment, for the compounds of formula (I), B is cyclopropyl, which is optionally substituted with a —(C$_1$-C$_6$ alkylene)$_m$-R$^{11}$ group.

In another embodiment, for the compounds of formula (I), B is cyclobutyl, which is optionally substituted with a —(C$_1$-C$_6$ alkylene)$_m$-R$^{11}$ group.

In another embodiment, for the compounds of formula (I), B is cycloheptyl, which is optionally substituted with a —(C$_1$-C$_6$ alkylene)$_m$-R$^{11}$ group.

In one embodiment, X is —CH$_2$—.
In another embodiment, X is —CH(CH$_3$)—.
In one embodiment, Y is —N(R$^3$)—.
In another embodiment, Y is —N(C$_1$-C$_6$ alkyl)-.
In another embodiment, Y is —N(CH$_3$)—.
In still another embodiment, Y is —CH(R$^6$)—.
In another embodiment, Y is —CH$_2$—.
In one embodiment, Y is —N(R$^3$)—, wherein R$^3$ is —(C$_1$-C$_6$ alkylene)$_m$-Z—(C$_1$-C$_3$ alkylene)$_m$-R$^{11}$.
In another embodiment, Y is —N(R$^3$)—, wherein R$^3$ is —(C$_1$-C$_6$ alkylene)-R$^{11}$.
In another embodiment, Y is —N(R$^3$)—, wherein R$^3$ is —(C$_1$-C$_6$ alkylene)-P(O)(—OR$^{18}$)$_2$.
In still another embodiment, Y is —N(R$^3$)—, wherein R$^3$ is —(C$_1$-C$_3$ alkylene)-P(O)(—OH)$_2$.
In another embodiment, Y is —N(R$^3$)—, wherein R$^3$ is —(C$_1$-C$_3$ alkylene)-P(O)(—OR$^{18}$)$_2$ and each occurrence of R$^{18}$ is C$_1$-C$_6$ alkyl.
In another embodiment, Y is —N(R$^3$)—, wherein R$^3$ is —(C$_1$-C$_3$ alkylene)-P(O)(—OR$^{18}$)$_2$ and each occurrence of R$^{18}$ is independently selected from H and —(C$_1$-C$_3$ alkylene)-OCC(O)O—(C$_1$-C$_6$ alkyl).
In yet another embodiment, Y is —N(R$^3$)—, wherein R$^3$ is —(C$_1$-C$_6$ alkylene)-R$^{11}$ and R$^{11}$ is:

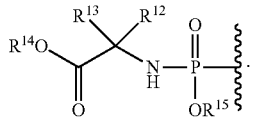

In another embodiment, Y is —N(R$^3$)—, wherein R$^3$ is —(C$_1$-C$_6$ alkylene)-R$^{11}$; R$^{11}$ is:

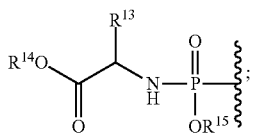

R$^{13}$ is C$_1$-C$_6$ alkyl; R$^{14}$ is C$_1$-C$_6$ alkyl; and R$^{15}$ is phenyl.

In one embodiment, R$^1$ is —(C$_1$-C$_6$ alkylene)$_m$-Z—(C$_1$-C$_3$ alkylene)$_m$-R$^{11}$.
In another embodiment, R$^1$ is —(C$_1$-C$_6$ alkylene)-R$^{11}$.
In another embodiment, R$^1$ is —(C$_1$-C$_6$ alkylene)-P(O)(—OR$^{18}$)$_2$.
In still another embodiment, R$^1$ is —(C$_1$-C$_3$ alkylene)-P(O)(—OF)$_2$.
In another embodiment, R$^1$ is —(C$_1$-C$_3$ alkylene)-P(O)(—OR$^{18}$)$_2$ and each occurrence of R$^{18}$ is C$_1$-C$_6$ alkyl.
In another embodiment, R$^1$ is —(C$_1$-C$_3$ alkylene)-P(O)(—OR$^{18}$)$_2$ and each occurrence of R$^{18}$ is independently selected from H and —(C$_1$-C$_3$ alkylene)-OC(O)O—(C$_1$-C$_6$ alkyl).
In yet another embodiment, R$^1$ is —(C$_1$-C$_6$ alkylene)-R$^{11}$ and R$^{11}$ is:

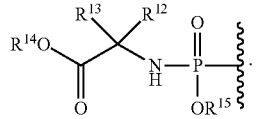

In another embodiment, R$_1$ is —(C$_1$-C$_6$ alkylene)-R$^{11}$; R$^{11}$ is:

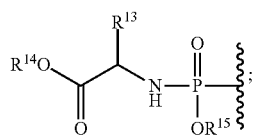

R$^{13}$ is C$_1$-C$_6$ alkyl; R$^{14}$ is C$_1$-C$_6$ alkyl; and R$^{15}$ is phenyl.
In one embodiment, R$^{th}$ is H.
In another embodiment, R$^{th}$ is —C$_3$-C$_7$ cycloalkyl.
In another embodiment, R$^{th}$ is —(C$_1$-C$_4$ alkylene)-O—(C$_1$-C$_6$ alkyl).
In another embodiment, R$^{th}$ is —CH$_2$OCH$_3$.
In one embodiment, the compounds of formula (I) have the formula (Ia):

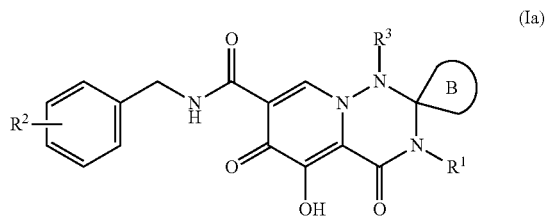

or a pharmaceutically acceptable salt or prodrug thereof, wherein:
B is cyclopentyl or cyclohexyl, optionally substituted with R$^6$;
R$^1$ is C$_1$-C$_6$ alkyl or —(C$_1$-C$_6$ alkylene)-R$^{11}$;
R$^2$ represents up to 2 optional substituents, each independently selected from halo; and
R$^3$ is C$_1$-C$_6$ alkyl or —(C$_1$-C$_6$ alkylene)-R$^{11}$;
R$^6$ is —(C$_1$-C$_6$ alkylene)$_m$-R$^{11}$;
each occurrence of R$^{11}$ is independently selected from —P(O)(—OR$^{18}$)$_2$ and:

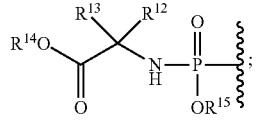

R$^{12}$ is independently selected from H and C$_1$-C$_6$ alkyl;
R$^{13}$ is independently selected from H and C$_1$-C$_6$ alkyl;
R$^{14}$ is C$_1$-C$_6$ alkyl;
R$^{15}$ is C$_6$-C$_{10}$ aryl;
each occurence of R$^{18}$ is independently selected from H and C$_1$-C$_6$ alkyl; and
m is 0 or 1, such that at least one occurrence of R$^{11}$ must be present in the compound of formula (I).
In one embodiment, for the compounds of formula (I) or (Ia), B is cyclopentyl, which is optionally substituted with a —(C$_1$-C$_6$ alkylene)$_q$-R$^{11}$ group.

In another embodiment, for the compounds of formula (I) or (Ia), B is cyclohexyl, which is optionally substituted with a —$(C_1\text{-}C_6 \text{ alkylene})_q\text{-}R^{11}$ group.

In one embodiment, for the compounds of formula (I) or (Ia), $R^1$ is $C_1\text{-}C_6$ alkyl.

In another embodiment, for the compounds of formula (I) or (Ia), $R^1$ is selected from methyl, ethyl and n-propyl.

In another embodiment, for the compounds of formula (I) or (Ia), $R^1$ is —$(C_1\text{-}C_6 \text{ alkylene})\text{-}R^{11}$.

In one embodiment, for the compounds of formula (I) or (Ia), each occurrence of $R^2$ is halo.

In another embodiment, for the compounds of formula (I) or (Ia), $R^2$ represents 2 fluoro groups.

In another embodiment, for the compounds of formula (I) or (Ia), $R^2$ represents 2 fluoro groups in the ortho and para positions.

In another embodiment, for the compounds of formula (I) or (Ia), $R^3$ is —$(C_1\text{-}C_6 \text{ alkylene})_m\text{-}R^{11}$.

In another embodiment, for the compounds of formula (I) or (Ia), $R^3$ is —$(C_1\text{-}C_6 \text{ alkylene})\text{-}P(O)(\text{—}OR^{18})_2$.

In still another embodiment, for the compounds of formula (I) or (Ia), $R^3$ is —$(C_1\text{-}C_3 \text{ alkylene})\text{-}P(O)(\text{—}OH)_2$.

In another embodiment, for the compounds of formula (I) or (Ia), $R^3$ is —$(C_1\text{-}C_3 \text{ alkylene})\text{-}P(O)(\text{—}OR^{18})_2$ and each occurrence of $R^{18}$ is $C_1\text{-}C_6$ alkyl.

In another embodiment, for the compounds of formula (I) or (Ia), $R^3$ is —$(C_1\text{-}C_3 \text{ alkylene})\text{-}P(O)(\text{—}OR^{18})_2$ and each occurrence of $R^{18}$ is independently selected from H and —$(C_1\text{-}C_3 \text{ alkylene})\text{-}OC(O)O\text{—}(C_1\text{-}C_6 \text{ alkyl})$.

In yet another embodiment, for the compounds of formula (I) or (Ia), $R^3$ is —$(C_1\text{-}C_6 \text{ alkylene})\text{-}R^{11}$ and $R^{11}$ is:

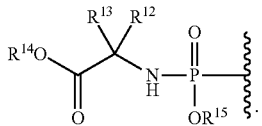

In another embodiment, for the compounds of formula (I) or (Ia), $R^3$ is —$(C_1\text{-}C_6 \text{ alkylene})\text{-}R^{11}$; $R^{11}$ is:

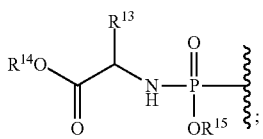

$R^{13}$ is $C_1\text{-}C_6$ alkyl; $R^{14}$ is $C_1\text{-}C_6$ alkyl; and $R^{15}$ is phenyl.

In one embodiment, variables B, X, Y, R, $R^1$, $R^2$ and $R^{10}$ for the Compounds of Formula (I) are selected independently of each other.

In one embodiment, the Compounds of Formula (I) are in substantially purified form.

Other embodiments of the present invention include the following:

(a) A pharmaceutical composition comprising an effective amount of a Compound of Formula (I) or a pharmaceutically acceptable salt or prodrug thereof, and a pharmaceutically acceptable carrier.

(b) The pharmaceutical composition of (a), further comprising a second therapeutic agent selected from the group consisting of HIV antiviral agents, immunomodulators, and anti-infective agents.

(c) The pharmaceutical composition of (b), wherein the HIV antiviral agent is an antiviral selected from the group consisting of HIV protease inhibitors, HIV integrase inhibitors, nucleoside reverse transcriptase inhibitors, CCR5 co-receptor antagonists and non-nucleoside reverse-transcriptase inhibitors.

(d) A pharmaceutical combination that is (i) a Compound of Formula (I) and (ii) a second therapeutic agent selected from the group consisting of HIV antiviral agents, immunomodulators, and anti-infective agents; wherein the Compound of Formula (I) and the second therapeutic agent are each employed in an amount that renders the combination effective for inhibiting HIV replication, or for treating HIV infection and/or reducing the likelihood or severity of symptoms of HIV infection.

(e) The combination of (d), wherein the HIV antiviral agent is an antiviral selected from the group consisting of HIV protease inhibitors, nucleoside reverse transcriptase inhibitors, CCR5 co-receptor antagonists, fusion and non-nucleoside reverse-transcriptase inhibitors.

(f) A method of inhibiting HIV replication in a subject in need thereof which comprises administering to the subject an effective amount of a Compound of Formula (I).

(g) A method of treating HIV infection and/or reducing the likelihood or severity of symptoms of HIV infection in a subject in need thereof which comprises administering to the subject an effective amount of a Compound of Formula (I).

(h) The method of (g), wherein the Compound of Formula (I) is administered in combination with an effective amount of at least one second therapeutic agent selected from the group consisting of HIV antiviral agents, immunomodulators, and anti-infective agents.

The method of (h), wherein the HIV antiviral agent is an antiviral selected from the group consisting of HIV protease inhibitors, nucleoside reverse transcriptase inhibitors, CCR5 co-receptor antagonists, fusion and non-nucleoside reverse-transcriptase inhibitors.

(j) A method of inhibiting HIV replication in a subject in need thereof which comprises administering to the subject the pharmaceutical composition of (a), (b) or (c) or the combination of (d) or (e).

(k) A method of treating HIV infection and/or reducing the likelihood or severity of symptoms of HIV infection in a subject in need thereof which comprises administering to the subject the pharmaceutical composition of (a), (b) or (c) or the combination of (d) or (e).

The present invention also includes a compound of the present invention for use (i) in, (ii) as a medicament for, or (iii) in the preparation of a medicament for: (a) medicine, (b) inhibiting HIV replication or (c) treating HIV infection and/or reducing the likelihood or severity of symptoms of HIV infection. In these uses, the compounds of the present invention can optionally be employed in combination with one or more second therapeutic agents selected from HIV antiviral agents, anti-infective agents, and immunomodulators.

Additional embodiments of the invention include the pharmaceutical compositions, combinations and methods set forth in (a)-(k) above and the uses set forth in the preceding paragraph, wherein the compound of the present invention employed therein is a compound of one of the embodiments, aspects, classes, sub-classes, or features of the compounds described above. In all of these embodiments, the compound may optionally be used in the form of a pharmaceutically acceptable salt or hydrate as appropriate. It is understood that references to compounds would include the compound in its present form as well as in different forms, such as polymorphs, solvates and hydrates, as applicable.

It is further to be understood that the embodiments of compositions and methods provided as (a) through (k) above are understood to include all embodiments of the compounds, including such embodiments as result from combinations of embodiments.

The Compounds of Formula (I) may be referred to herein by chemical structure and/or by chemical name. In the instance that both the structure and the name of a Compound of Formula (I) are provided and a discrepancy is found to exist between the chemical structure and the corresponding chemical name, it is understood that the chemical structure will predominate.

Non-limiting examples of the Compounds of Formula (I) include compounds 1-9, 20-37, 8a, 8b and 18b as set forth in the Examples below, and pharmaceutically acceptable salts thereof.

Uses of the Pyridotriazine Derivatives

The Amido-Substituted Pyridotriazine Derivatives may be useful in human and veterinary medicine for treating or preventing HIV infection in a subject. In one embodiment, the Amido-Substituted Pyridotriazine Derivatives may be inhibitors of HIV viral replication. In a specific embodiment, the Amido-Substituted Pyridotriazine Derivatives are inhibitors of HIV-1. Accordingly, the Amido-Substituted Pyridotriazine Derivatives may be useful for treating HIV infections and AIDS. In accordance with the invention, the Amido-Substituted Pyridotriazine Derivatives may be administered to a subject in need of treatment or prevention of HIV infection.

Accordingly, in one embodiment, the invention provides methods for treating HIV infection in a subject comprising administering to the subject an effective amount of at least one Amido-Substituted Pyridotriazine Derivative or a pharmaceutically acceptable salt or prodrug thereof. In a specific embodiment, the present invention provides methods for treating AIDS in a subject comprising administering to the subject an effective amount of at least one Amido-Substituted Pyridotriazine Derivative or a pharmaceutically acceptable salt or prodrug thereof.

Treatment or Prevention of HIV Infection

The Amido-Substituted Pyridotriazine Derivatives may be useful in the inhibition of HIV, the treatment of HIV infection and/or reduction of the likelihood or severity of symptoms of HIV infection and the inhibition of HIV viral replication and/or HIV viral production in a cell-based system. For example, the Amido-Substituted Pyridotriazine Derivatives may be useful in treating infection by HIV after suspected past exposure to HIV by such means as blood transfusion, exchange of body fluids, bites, accidental needle stick, or exposure to subject blood during surgery or other medical procedures.

In one embodiment, the HIV infection has progressed to AIDS.

Accordingly, in one embodiment, the invention provides methods for treating HIV infection in a subject, the methods comprising administering to the subject an effective amount of at least one Amido-Substituted Pyridotriazine Derivative or a pharmaceutically acceptable salt or prodrug thereof. In a specific embodiment, the amount administered is effective to treat or prevent infection by HIV in the subject. In another specific embodiment, the amount administered is effective to inhibit HIV viral replication and/or viral production in the subject.

The Amido-Substituted Pyridotriazine Derivatives may also be useful in the preparation and execution of screening assays for antiviral compounds. For example the Amido-Substituted Pyridotriazine Derivatives may be useful for identifying resistant HIV cell lines harboring mutations, which are excellent screening tools for more powerful antiviral compounds. Furthermore, the Amido-Substituted Pyridotriazine Derivatives may be useful in establishing or determining the binding site of other antivirals to the HIV Integrase.

Combination Therapy

In another embodiment, the present methods for treating or preventing HIV infection can further comprise the administration of one or more additional therapeutic agents which are not Amido-Substituted Pyridotriazine Derivatives.

In one embodiment, the additional therapeutic agent is an antiviral agent.

In another embodiment, the additional therapeutic agent is an immunomodulatory agent, such as an immunosuppressive agent.

Accordingly, in one embodiment, the present invention provides methods for treating a viral infection in a subject, the method comprising administering to the subject: (i) at least one Amido-Substituted Pyridotriazine Derivative (which may include two or more different Amido-Substituted Pyridotriazine Derivatives), or a pharmaceutically acceptable salt or prodrug thereof, and (ii) at least one additional therapeutic agent that is other than an Amido-Substituted Pyridotriazine Derivative, wherein the amounts administered are together effective to treat or prevent a viral infection.

When administering a combination therapy of the invention to a subject, therapeutic agents in the combination, or a pharmaceutical composition or compositions comprising therapeutic agents, may be administered in any order such as, for example, sequentially, concurrently, together, simultaneously and the like. The amounts of the various actives in such combination therapy may be different amounts (different dosage amounts) or same amounts (same dosage amounts). Thus, for non-limiting illustration purposes, an Amido-Substituted Pyridotriazine Derivative and an additional therapeutic agent may be present in fixed amounts (dosage amounts) in a single dosage unit (e.g., a capsule, a tablet and the like).

In one embodiment, the at least one Amido-Substituted Pyridotriazine Derivative is administered during a time when the additional therapeutic agent(s) exert their prophylactic or therapeutic effect, or vice versa.

In another embodiment, the at least one Amido-Substituted Pyridotriazine Derivative and the additional therapeutic agent(s) are administered in doses commonly employed when such agents are used as monotherapy for treating a viral infection.

In another embodiment, the at least one Amido-Substituted Pyridotriazine Derivative and the additional therapeutic agent(s) are administered in doses lower than the doses commonly employed when such agents are used as monotherapy for treating a viral infection.

In still another embodiment, the at least one Amido-Substituted Pyridotriazine Derivative and the additional therapeutic agent(s) act synergistically and are administered in doses lower than the doses commonly employed when such agents are used as monotherapy for treating a viral infection.

In one embodiment, the at least one Amido-Substituted Pyridotriazine Derivative and the additional therapeutic agent(s) are present in the same composition. In one embodiment, this composition is suitable for oral administration. In another embodiment, this composition is suitable for intravenous administration. In another embodiment, this composition is suitable for subcutaneous administration. In still another embodiment, this composition is suitable for parenteral administration.

Viral infections and virus-related disorders that may be treated or prevented using the combination therapy methods of the present invention include, but are not limited to, those listed above.

In one embodiment, the viral infection is HIV infection.

In another embodiment, the viral infection is HIV infection which has progressed to AIDS.

The at least one Amido-Substituted Pyridotriazine Derivative and the additional therapeutic agent(s) can act additively or synergistically. A synergistic combination may allow the use of lower dosages of one or more agents and/or less frequent administration of one or more agents of a combination therapy. A lower dosage or less frequent administration of one or more agents may lower toxicity of therapy without reducing the efficacy of therapy.

In one embodiment, the administration of at least one Amido-Substituted Pyridotriazine Derivative and the additional therapeutic agent(s) may inhibit the resistance of a viral infection to these agents.

As noted above, the present invention is also directed to use of a compound of Formula I with one or more anti-HIV agents. An "anti-HIV agent" is any agent which is directly or indirectly effective in the inhibition of HIV reverse transcriptase or another enzyme required for HIV replication or infection, the treatment or prophylaxis of HIV infection, and/or the treatment, prophylaxis or delay in the onset or progression of AIDS. It is understood that an anti-HIV agent is effective in treating, preventing, or delaying the onset or progression of HIV infection or AIDS and/or diseases or conditions arising therefrom or associated therewith. For example, the compounds of this invention may be effectively administered, whether at periods of pre-exposure and/or post-exposure, in combination with effective amounts of one or more anti-HIV agents selected from HIV antiviral agents, imunomodulators, antiinfectives, or vaccines useful for treating HIV infection or AIDS. Suitable HIV antivirals for use in combination with the compounds of the present invention include, for example, those listed in Table A as follows:

TABLE A

| Name | Type |
|---|---|
| abacavir, ABC, Ziagen ® | nRTI |
| abacavir + lamivudine, Epzicom ® | nRTI |
| abacavir + lamivudine + zidovudine, Trizivir ® | nRTI |
| amprenavir, Agenerase ® | PI |
| atazanavir, Reyataz ® | PI |
| AZT, zidovudine, azidothymidine, Retrovir ® | nRTI |
| CMX-157 | nRTI |
| darunavir, Prezista ® | PI |
| ddC, zalcitabine, dideoxycytidine, Hivid ® | nRTI |
| ddI, didanosine, dideoxyinosine, Videx ® | nRTI |
| ddI (enteric coated), Videx EC ® | nRTI |
| delavirdine, DLV, Rescriptor ® | nnRTI |
| Dolutegravir | PI |
| efavirenz, EFV, Sustiva ®, Stocrin ® | nnRTI |
| efavirenz + emtricitabine + tenofovir DF, Atripla ® | nnRTI + nRTI |
| Elvitegravir | InI |
| emtricitabine, FTC, Emtriva ® | nRTI |
| emtricitabine + tenofovir DF, Truvada ® | nRTI |
| emvirine, Coactinon ® | nnRTI |

TABLE A-continued

| Name | Type |
|---|---|
| enfuvirtide, Fuzeon ® | FI |
| enteric coated didanosine, Videx EC ® | nRTI |
| etravirine, TMC-125 | nnRTI |
| fosamprenavir calcium, Lexiva ® | PI |
| indinavir, Crixivan ® | PI |
| lamivudine, 3TC, Epivir ® | nRTI |
| lamivudine + zidovudine, Combivir ® | nRTI |
| lopinavir | PI |
| lopinavir + ritonavir, Kaletra ® | PI |
| maraviroc, Selzentry ® | EI |
| nelfinavir, Viracept ® | PI |
| nevirapine, NVP, Viramune ® | nnRTI |
| raltegravir, MK-0518, Isentress ® | InI |
| rilpivirine, TMC-278 | nnRTI |
| Rilpivirine + emtricitabine + tenofovir, Complera | nnRTI + nRTI |
| ritonavir, Norvir ® | PI |
| saquinavir, Invirase ®, Fortovase ® | PI |
| stavudine, d4T,didehydrodeoxythymidine, Zerit ® | nRTI |
| tenofovir DF (DF = disoproxil fumarate), TDF, Viread ® | nRTI |
| tipranavir, Aptivus ® | PI |

EI = entry inhibitor;
FI = fusion inhibitor;
InI = integrase inhibitor;
PI = protease inhibitor;
nRTI = nucleoside reverse transcriptase inhibitor;
nnRTI = non-nucleoside reverse transcriptase inhibitor.
Some of the drugs listed in the table are used in a salt form; e.g., abacavir sulfate, indinavir sulfate, atazanavir sulfate, nelfinavir mesylate.

In one embodiment, the one or more anti-HIV drugs are selected from raltegravir, lamivudine, abacavir, ritonavir, darunavir, atazanavir, emtricitabine, tenofovir, elvitegravir, rilpivirine and lopinavir.

In another embodiment, the compound of formula (I) is used in combination with a single anti-HIV drug which is lamivudine.

In still another embodiment, the compound of formula (I) is used in combination with a single anti-HIV drug which is atazanavir.

In another embodiment, the compound of formula (I) is used in combination with a single anti-HIV drug which is darunavir.

In another embodiment, the compound of formula (I) is used in combination with a single anti-HIV drug which is rilpivirine.

In one embodiment, the compound of formula (I) is used in combination with two anti-HIV drugs which are lamivudine and abacavir.

In another embodiment, the compound of formula (I) is used in combination with two anti-HIV drugs which are emtricitabine and tenofovir.

In another embodiment, the compound of formula (I) is used in combination with two anti-HIV drugs which are ritonavir and lopinavir.

In one embodiment, the present invention provides pharmaceutical compositions comprising (i) a compound of formula (I) or a pharmaceutically acceptable salt or prodrug thereof; (ii) a pharmaceutically acceptable carrier; and (iii) one or more additional anti-HIV agents selected from lamivudine, abacavir, ritonavir and lopinavir, or a pharmaceutically acceptable salt thereof, wherein the amounts present of components (i) and (iii) are together effective for the treatment or prophylaxis of infection by HIV or for the treatment, prophylaxis, or delay in the onset or progression of AIDS in the subject in need thereof.

In another embodiment, the present invention provides a method for the treatment or prophylaxis of infection by HIV or for the treatment, prophylaxis, or delay in the onset or progression of AIDS in a subject in need thereof, which comprises administering to the subject (i) a compound of formula (I) or a pharmaceutically acceptable salt or prodrug thereof and (ii) one or more additional anti-HIV agents selected from lamivudine, abacavir, ritonavir and lopinavir, or a pharmaceutically acceptable salt thereof, wherein the amounts administered of components (i) and (ii) are together effective for the treatment or prophylaxis of infection by HIV or for the treatment, prophylaxis, or delay in the onset or progression of AIDS in the subject in need thereof.

It is understood that the scope of combinations of the compounds of this invention with anti-HIV agents is not limited to the HIV antivirals listed in Table A, but includes in principle any combination with any pharmaceutical composition useful for the treatment or prophylaxis of AIDS. The HIV antiviral agents and other agents will typically be employed in these combinations in their conventional dosage ranges and regimens as reported in the art, including, for example, the dosages described in the *Physicians' Desk Reference*, Thomson PDR, Thomson PDR, $57^{th}$ edition (2003), the $58^{th}$ edition (2004), the $59^{th}$ edition (2005), and the like. The dosage ranges for a compound of the invention in these combinations are the same as those set forth above.

The compounds of this invention may also be useful in the preparation and execution of screening assays for antiviral compounds. For example, the compounds of this invention are useful for isolating enzyme mutants, which are excellent screening tools for more powerful antiviral compounds. Furthermore, the compounds of this invention are useful in establishing or determining the binding site of other antivirals to HIV integrase, e.g., by competitive inhibition. Thus the compounds of this invention are commercial products to be sold for these purposes.

The doses and dosage regimen of the other agents used in the combination therapies of the present invention for the treatment or prevention of HIV infection may be determined by the attending clinician, taking into consideration the approved doses and dosage regimen in the package insert; the age, sex and general health of the subject; and the type and severity of the viral infection or related disease or disorder. When administered in combination, the Amido-Substituted Pyridotriazine Derivative(s) and the other agent(s) may be administered simultaneously (i.e., in the same composition or in separate compositions one right after the other) or sequentially. This particularly useful when the components of the combination are given on different dosing schedules, e.g., one component is administered once daily and another component is administered every six hours, or when the pharmaceutical compositions are different, e.g., one is a tablet and one is a capsule. A kit comprising the separate dosage forms is therefore advantageous.

Compositions and Administration

When administered to a subject, the Amido-Substituted Pyridotriazine Derivatives may be administered as a component of a composition that comprises a pharmaceutically acceptable carrier or vehicle. The present invention provides pharmaceutical compositions comprising an effective amount of at least one Amido-Substituted Pyridotriazine Derivative and a pharmaceutically acceptable carrier. In the pharmaceutical compositions and methods of the present invention, the active ingredients will typically be administered in admixture with suitable carrier materials suitably selected with respect to the intended form of administration, i.e., oral tablets, capsules (either solid-filled, semi-solid filled or liquid filled), powders for constitution, oral gels, elixirs, dispersible granules, syrups, suspensions, and the like, and consistent with conventional pharmaceutical practices. For example, for oral administration in the form of tablets or capsules, the active drug component may be combined with any oral non-toxic pharmaceutically acceptable inert carrier, such as lactose, starch, sucrose, cellulose, magnesium stearate, dicalcium phosphate, calcium sulfate, talc, mannitol, ethyl alcohol (liquid forms) and the like. Solid form preparations include powders, tablets, dispersible granules, capsules, cachets and suppositories. Powders and tablets may be comprised of from about 0.5 to about 95 percent inventive composition. Tablets, powders, cachets and capsules may be used as solid dosage forms suitable for oral administration.

Moreover, when desired or needed, suitable binders, lubricants, disintegrating agents and coloring agents may also be incorporated in the mixture. Suitable binders include starch, gelatin, natural sugars, corn sweeteners, natural and synthetic gums such as acacia, sodium alginate, carboxymethylcellulose, polyethylene glycol and waxes. Among the lubricants there may be mentioned for use in these dosage forms, boric acid, sodium benzoate, sodium acetate, sodium chloride, and the like. Disintegrants include starch, methylcellulose, guar gum, and the like. Sweetening and flavoring agents and preservatives may also be included where appropriate.

Liquid form preparations include solutions, suspensions and emulsions and may include water or water-propylene glycol solutions for parenteral injection.

Liquid form preparations may also include solutions for intranasal administration.

Also included are solid form preparations which are intended to be converted, shortly before use, to liquid form preparations for either oral or parenteral administration. Such liquid forms include solutions, suspensions and emulsions.

For preparing suppositories, a low melting wax such as a mixture of fatty acid glycerides or cocoa butter is first melted, and the active ingredient is dispersed homogeneously therein as by stirring. The molten homogeneous mixture is then poured into convenient sized molds, allowed to cool and thereby solidify.

Additionally, the compositions of the present invention may be formulated in sustained release form to provide the rate controlled release of any one or more of the components or active ingredients to optimize therapeutic effects, i.e., antiviral activity and the like. Suitable dosage forms for sustained release include layered tablets containing layers of varying disintegration rates or controlled release polymeric matrices impregnated with the active components and shaped in tablet form or capsules containing such impregnated or encapsulated porous polymeric matrices.

In one embodiment, the one or more Amido-Substituted Pyridotriazine Derivatives are administered orally.

In another embodiment, the one or more Amido-Substituted Pyridotriazine Derivatives are administered intravenously.

In one embodiment, a pharmaceutical preparation comprising at least one Amido-Substituted Pyridotriazine Derivative is in unit dosage form. In such form, the preparation is subdivided into unit doses containing effective amounts of the active components.

Compositions may be prepared according to conventional mixing, granulating or coating methods, respectively, and the present compositions can contain, in one embodiment, from about 0.1% to about 99% of the Amido-Substituted Pyridotriazine Derivative(s) by weight or volume. In various embodiments, the present compositions can contain, in one embodiment, from about 1% to about 70% or from about 5% to about 60% of the Amido-Substituted Pyridotriazine Derivative(s) by weight or volume.

The compounds of Formula I may be administered orally in a dosage range of 0.001 to 1000 mg/kg of mammal (e.g., human) body weight per day in a single dose or in divided doses. One dosage range is 0.01 to 500 mg/kg body weight per day orally in a single dose or in divided doses. Another dosage range is 0.1 to 100 mg/kg body weight per day orally in single or divided doses. For oral administration, the compositions may be provided in the form of tablets or capsules containing 1.0 to 500 milligrams of the active ingredient, particularly 1, 5, 10, 15, 20, 25, 50, 75, 100, 150, 200, 250, 300, 400, and 500 milligrams of the active ingredient for the symptomatic adjustment of the dosage to the subject to be treated. The specific dose level and frequency of dosage for any particular subject may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

For convenience, the total daily dosage may be divided and administered in portions during the day if desired. In one embodiment, the daily dosage is administered in one portion. In another embodiment, the total daily dosage is administered in two divided doses over a 24 hour period. In another embodiment, the total daily dosage is administered in three divided doses over a 24 hour period. In still another embodiment, the total daily dosage is administered in four divided doses over a 24 hour period.

The amount and frequency of administration of the Amido-Substituted Pyridotriazine Derivatives will be regulated according to the judgment of the attending clinician considering such factors as age, condition and size of the subject as well as severity of the symptoms being treated. The compositions of the invention can further comprise one or more additional therapeutic agents, selected from those listed above herein. Accordingly, in one embodiment, the present invention provides compositions comprising: (i) at least one Amido-Substituted Pyridotriazine Derivative or a pharmaceutically acceptable salt or prodrug thereof; (ii) one or more additional therapeutic agents that are not an Amido-Substituted Pyridotriazine Derivative; and (iii) a pharmaceutically acceptable carrier, wherein the amounts in the composition are together effective to treat HIV infection.

Kits

In one aspect, the present invention provides a kit comprising a therapeutically effective amount of at least one Amido-Substituted Pyridotriazine Derivative, or a pharmaceutically acceptable salt or prodrug of said compound and a pharmaceutically acceptable carrier, vehicle or diluent.

In another aspect the present invention provides a kit comprising an amount of at least one Amido-Substituted Pyridotriazine Derivative, or a pharmaceutically acceptable salt or prodrug of said compound and an amount of at least one additional therapeutic agent listed above, wherein the amounts of the two or more active ingredients result in a desired therapeutic effect. In one embodiment, the one or more Amido-Substituted Pyridotriazine Derivatives and the one or more additional therapeutic agents are provided in the same container. In one embodiment, the one or more Amido-Substituted Pyridotriazine Derivatives and the one or more additional therapeutic agents are provided in separate containers.

Methods for Making the Compounds of Formula (I)

The Compounds of Formula (I) may be prepared from known or readily prepared starting materials, following methods known to one skilled in the art of organic synthesis. Methods useful for making the Compounds of Formula (I) are set forth in the Examples below and generalized in the Schemes below. Alternative synthetic pathways and analogous structures will be apparent to those skilled in the art of organic synthesis.

The following schemes describe general methods for preparing the compounds of Formula (I).

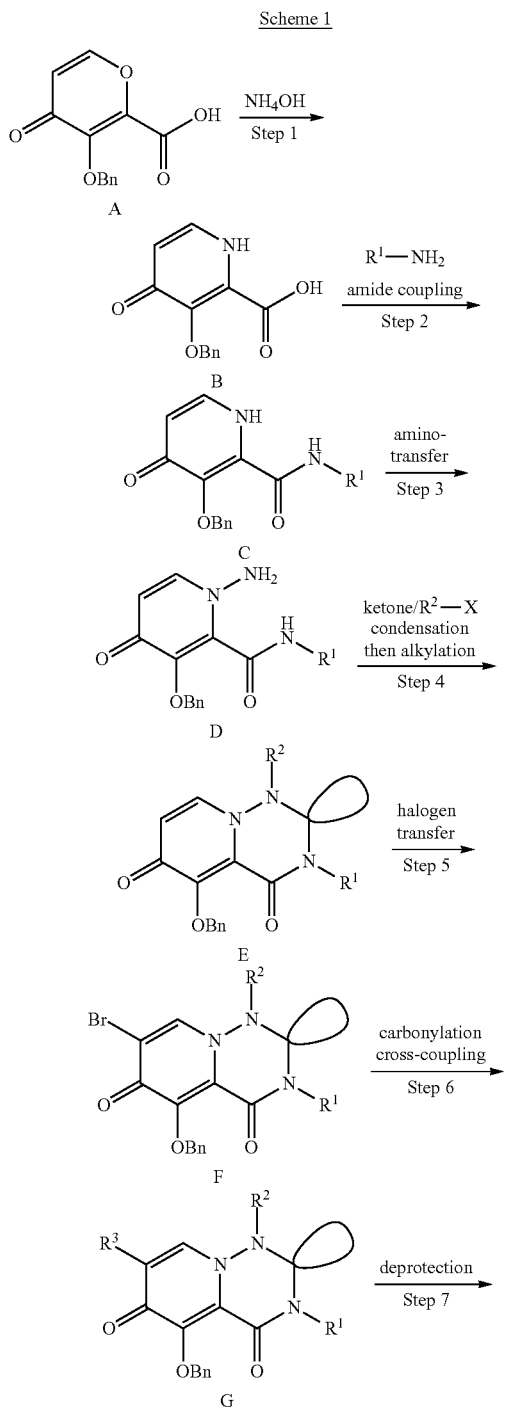

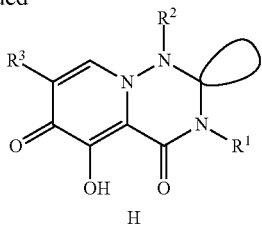

Scheme 1 shows a general route to prepare the compounds of this invention. A pyranone compound of formula A upon treatment with aqueous ammonium hydroxide affords a 4-pyridinone of formula B. Treatment of B with a suitably funtionalized amine under standard amide formation conditions affords C, which is subjected to an amino-transfer reagent to provide compound D. A two-step procedure involving condensation of hydrazide D with a carbocyclic or heterocyclic ketone followed by alkylation with a suitably functionalized alkylating reagent affords E. Halogen transfer to E affords F which is then subjected to carbonylation or cross-coupling to provide G. Deprotection of compound G affords compound hours.

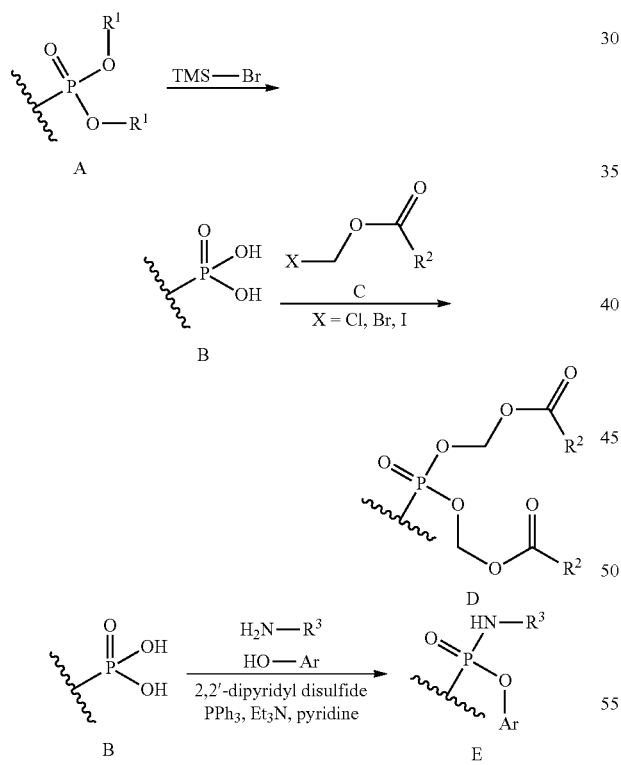

Scheme 2 shows some methods to prepare prodrugs of phosphonates. Prodrugs of phosphonates may be prepared from the dialkylphosphonate A which is converted to the phosphonic acid B. Phosphonic acid B may be converted to acetal prodrugs such as D by reaction with a suitably functionalized halide C under standard conditions. Phosphonic acid B can also be converted to prodrug E as shown under standard conditions.

IA
A
General Methods

The compounds described herein may be prepared according to the procedures of the following schemes and examples, using appropriate materials and are further exemplified by the following specific examples. The compounds illustrated in the examples are not, however, to be construed as forming the only genus that is considered as the invention. The examples further illustrate details for the preparation of the compounds of the present invention. Those skilled in the art will readily understand that known variations of the conditions and processes of the following preparative procedures may be used to prepare these compounds. Concentration refers to the removal of the volatile components at reduced pressure (e.g. rotary evaporation) unless otherwise noted. All temperatures are degrees Celsius unless otherwise noted. Mass spectra (MS) were measured by electrospray ion-mass spectroscopy (ESI) in positive ion detection mode and m/z refers to the [M+H]$^+$ ion unless otherwise noted. $^1$H NMR spectra were recorded at 400-500 MHz at ambient temparature unless otherwise noted. When the $^1$H NMR spectrum exhibits conformational isomers at room temperature, brackets { } indicate groups of signals that may be assigned to the same proton and integrations are not representative of any ratio. RP-HPLC refers to reverse-phase HPLC on C18-functionalized preparative or semi-preparative columns with gradient elution using acetonitrile and water modified with trifluoroacetic acid as eluents and fractions were lyophylized or concentrated by rotary evaporation unless otherwise noted. RP-MPLC refers to reverse phase medium pressure liquid chromatography using a flash chromatography system (e.g. ISCO or Biotage) and commercial pre-packed C18-functionalized silica gel columns with gradient elution using acetonitrile and water modified with trifluoroacetic acid as eluents and fractions were lyophylized or concentrated by rotary evaporation unless otherwise noted. Compounds described herein were synthesized as the racemates unless otherwise noted in the experimental procedures and compound tables. For stereoisomers, enantiomer A or diastereomer A refers to the earlier eluting enantiomer or diastereomer, respectively, and enantiomer B or diastereomer B refers to the later eluting enantiomer or diastereomer, respectively, at the point of chiral resolution and this nomenclature is maintained through the remainder of a synthetic sequence for a given enantiomeric or diastereomeric series regardless of the possibility that subsequent intermediates or final compounds may have the same or opposite orders of elution.

Example 1

Preparation of Compound 1

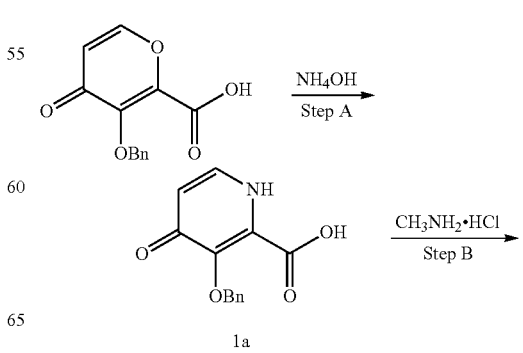

1a

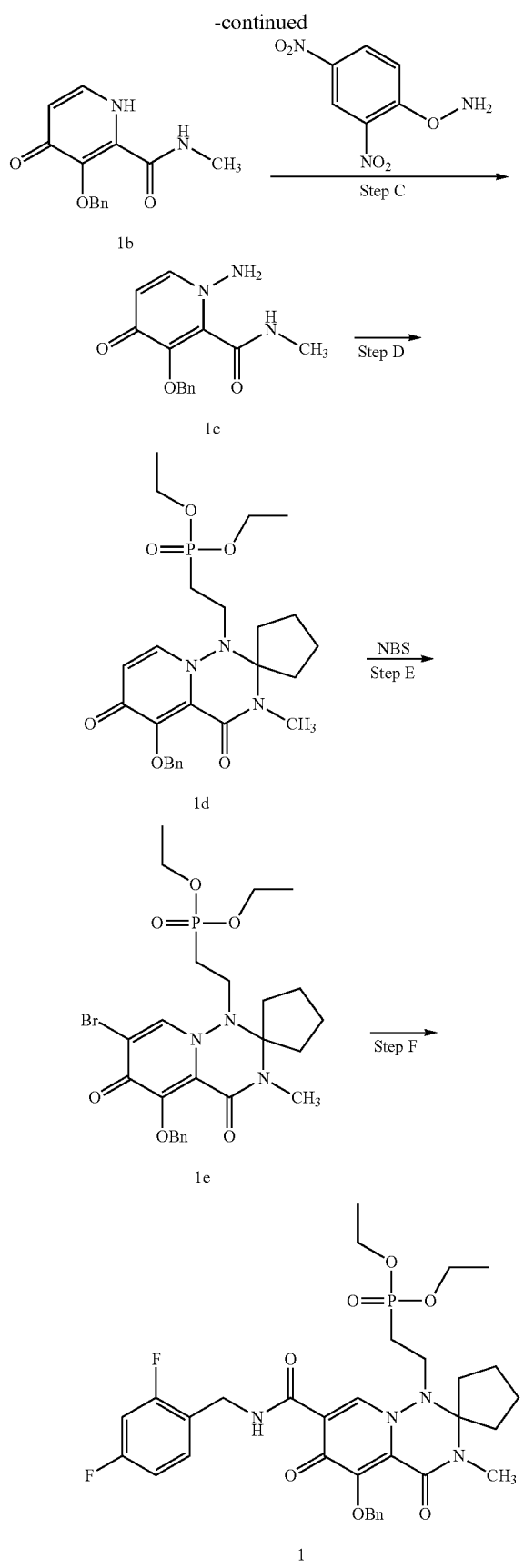

Step A—Synthesis of Intermediate Compound 1a 3-(benzyloxy)-4-oxo-4H-pyran-2-carboxylic acid (30.00 g, 122 mmol) was taken up in 28% aqueous ammonium hydroxide (150 ml, 1079 mmol) at room temperature and the mixture was allowed to stir at room temperature for 16 hours. The reaction mixture was diluted with water to a total volume of 500 mL and then treated with 36% aqueous HCl until the pH was approximately 4 and additional water (500 mL) was added. The reaction mixture was aged for 12 hours at room temperature. The solids were collected by filtration, washed with water (250 mL) and then dried under vacuum to provide intermediate compound 1a that was used without further purification. Mass (calculated) for $C_{13}H_{11}NO_4$: 245.1, found 246.1 (M+H)$^+$; $^1$H NMR: (400 MHz, DMSO-d6) δ 7.70 (bs, 1H), 7.43-7.45 (m, 2H), 7.27-7.35 (m, 3H), 6.53 (bs, 1H), 5.07 (s, 2H).

Step B—Synthesis of Intermediate Compound 1b

A mixture of 1a (20 g, 82 mmol) and HOBT (13.74 g, 90 mmol) in dichloromethane (100 mL) was cooled to 0° C. and treated with EDC (17.20 g, 90 mmol) and N-methylmorpholine (26.9 mL, 245 mmol). After 5 min of stirring, methanamine hydrochloride (6.06 g, 90 mmol) was added. The resulting reaction was allowed to stir for 20 hours while slowly warming to room temperature. The reaction mixture was concentrated in vacuo to provide a viscous syrup that was taken up in DMSO (30 mL), neutralized with glacial acetic acid and purified using RP-MPLC to provide intermediate compound 1b. Mass (calculated) for $C_{14}H_{14}N_2O_3$: 258.1, found 259.1 (M+H)$^+$; $^1$H NMR (500 MHz, DMSO) δ 8.40 (s, 1H), 7.62 (d, J=6.8 Hz, 1H), 7.30-7.39 (m, 5H), 6.42 (d, J=6.7 Hz, 1H), 5.32 (s, 2H), 2.74 (d, J=4.8 Hz, 3H).

Step C—Synthesis of Intermediate Compound 1c

A mixture of 1b (18.10 g, 70.1 mmol) and potassium carbonate (29.1 g, 210 mmol) in N,N-dimethylformamide (150 mL) at 0° C. was treated with O-(2,4-dinitrophenyl)hydroxylamine (27.9 g, 140 mmol) and was allowed to warm to room temperature and stir at room temperature for 48 hours. The reaction mixture was filtered through a pad of celite (acetonitrile rinse) and the filtrate was neutralized with glacial acetic acid. The resulting solution was directly purified using RP-MPLC to provide intermediate compound 1c that was used without further purification. Mass (calculated) for $C_{14}H_{15}N_3O_3$: 273.1, found 274.2 (M+H)$^+$; $^1$H NMR (500 MHz, CDCl$_3$): δ 7.61 (bs, 1H), 7.42 (d, J=7.6 Hz, 1H), 7.31-7.35 (m, 5H), 6.24 (d, J=7.6 Hz, 1H), 5.07 (s, 2H), 2.64 (d, J=4.9 Hz, 3H).

Step D—Synthesis of Intermediate Compound 1d

A solution of intermediate 1c (2.00 g, 7.32 mmol) in dioxane (20.0 mL) was treated at room temperature with cyclopentanone (3.24 ml, 36.6 mmol) and glacial acetic acid (0.050 mL). The reaction mixture was allowed to stir at room temperature for 16 hours and then directly applied to a dry prepacked silica gel column. Purification by column chromatography on silica gel (0 to 30% MeOH/dichloromethane) provided an intermediate compound. This intermediate compound was taken up in DMSO (20 mL) and treated with diethyl 2-bromoethylphosphonate (2.66 ml, 14.64 mmol), tetrabutylammonium hydroxide, triacontahydrate (0.585 g, 0.732 mmol) and potassium hydroxide (1.232 g, 21.95 mmol). The reaction mixture was allowed to stir at room temperature for 3 hours, neutralized with glacial acetic acid and directly purified using RP-HPLC to provide intermediate compound 1d. Mass (calculated) for $C_{25}H_{34}N_3O_6P$: 503.2, found 504.5 (M+H)$^+$.

Step E—Synthesis of Intermediate Compound 1e

To a solution of intermediate compound id (2.602 g, 5.17 mmol) in N,N-dimethylformamide (10 mL) was added N-bromosuccinimide (1.839 g, 10.34 mmol). The resulting resulting reaction was allowed to stir at room temperature for 3 hours, then the reaction mixture was directly purified using RP-MPLC to provide intermediate compound 1e. Mass (calculated) for $C_{25}H_{33}BrN_3O_6P$: 581.1, 583.1 found 582.2, 584.2 $(M+H)^+$.

Step F—Synthesis of Intermediate Compound 1

Intermediate compound 1e (2.47 g, 4.24 mmol) in DMSO (10.0 mL) was sub-surface sparged with nitrogen gas for 10 minutes at room temperature and to the resulting solution was added 2,4-difluorophenylmethanamine (1.512 ml, 12.72 mmol), N,N-diisopropylethylamine (1.481 ml, 8.48 mmol) and $Pd(Ph_3P)_4$ (0.980 g, 0.848 mmol). The resulting resulting reaction was heated at 90° C. and allowed to stir at this temperature for 8 hours under CO (1 atm), then the reaction mixture was allowed to cooled to room temperature and filtered. The filtrate was directly purified using RP-HPLC to provide intermediate compound 1. Mass (calculated) for $C_{33}H_{39}F_2N_4O_7P$: 672.3 found 673.4 $(M+H)^+$; $^1H$ NMR (500 MHz, $CDCl_3$): δ 10.46 (s; 1H); 8.47 (s; 1H); 7.51-7.51 (m; 2H); 7.38-7.41 (m; 1H); 7.26-7.32 (m; 3H); 6.81-6.86 (m; 2H); 5.51 (t; J=9.5 Hz; 1H); 5.25 (t; J=9.5 Hz; 1H); 4.65 (s; 2H); 4.06-4.14 (m; 4H); 3.33 (br s; 1H); 3.08 (d; J=8.7 Hz; 3H); 2.91-2.96 (m; 1H); 2.24-2.26 (m; 1H); 1.97-2.04 (br m; 4H); 1.60-1.79 (br m; 6H); 1.29-1.39 (m; 4H); 1.20-1.24 (br m; 1H).

Example 2

Preparation of Compound 2

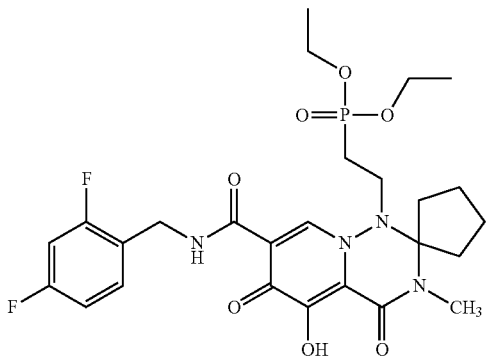

Compound 1 (65 mg, 0.097 mmol) was stirred in TFA (1.0 mL) at room temperature for 14 hours, diluted with acetonitrile and directly purified using RP-HPLC to provide compound 2. Mass (calculated) for $C_{26}H_{33}F_2N_4O_7P$: 582.2 found 583.4 $(M+H)^+$; $^1H$ NMR (500 MHz, $CDCl_3$): δ 10.45 (s; 1H); 8.48 (s; 1H); 7.38 (q; J=7.6 Hz; 1H); 6.79-6.85 (m; 2H); 4.66 (qd; J=15.3, 5.4 Hz; 2H); 4.07-4.18 (m; 4H); 3.40-3.48 (m; 1H); 3.15 (s; 3H); 2.95-3.02 (m; 1H); 2.32-2.36 (m; 1H); 2.11-2.17 (m; 1H); 1.94-2.06 (m; 3H); 1.88 (t; J=7.5 Hz; 1H); 1.76-1.81 (m; 2H); 1.63-1.71 (m; 2H); 1.37 (t; J=7.1 Hz; 3H); 1.31 (t; J=7.1 Hz; 3H).

Example 3

Preparation of Compound 3

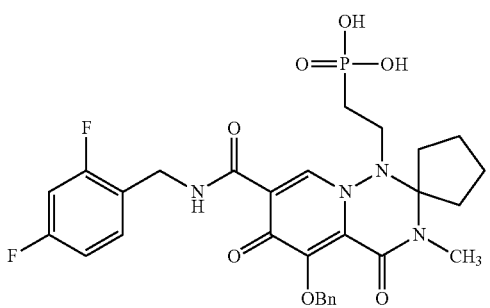

Compound 1 (1.7375 g, 2.58 mmol) in acetonitrile (10 mL) was treated at room temperature with 2,6-lutidine (1.203 ml, 10.33 mmol) and trimethylsilyl bromide (1.005 ml, 7.75 mmol). The reaction mixture was allowed to stir at room temperature for 6 hours, quenched with water (0.5 mL) at room temperature, diluted with acetonitrile and directly purified using RP-HPLC to provide compound 3. Mass (calculated) for $C_{29}H_{31}F_2N_4O_7P$: 616.2 found 617.4 $(M+H)^+$; $^1H$ NMR (500 MHz, $CD_3OD$): δ 8.51 (s; 1H); 7.45 (q; J=7.8 Hz; 1H); 7.34 (d; J=5.9 Hz; 2H); 7.27 (d; J=5.2 Hz; 3H); 6.93-7.00 (m; 2H); 5.46 (d; J=10.9 Hz; 1H); 5.21 (d; J=10.9 Hz; 1H); 4.60-4.68 (m; 2H); 3.33-3.41 (m; 1H); 3.07 (s; 3H); 2.84-2.91 (m; 1H); 2.32-2.37 (m; 1H); 2.04-2.13 (m; 1H); 1.94-2.00 (m; 2H); 1.81-1.85 (m; 1H); 1.55-1.76 (m; 3H); 1.40-1.46 (m; 1H); 0.97-1.02 (m; 1H).

Example 4

Preparation of Compound 4

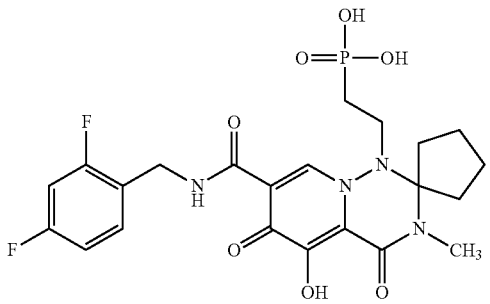

Compound 3 (100 mg, 0.162 mmol) in TFA (1.5 mL) was allowed to stir at room temperature for 14 hours. The Mixture was diluted with acetonitrile and directly purified using RP-HPLC to provide compound 4. Mass (calculated) for $C_{22}H_{25}F_2N_4O_7P$: 526.1 found 527.3 $(M+H)^+$; $^1H$ NMR (500 MHz, $CD_3OD$): δ 8.54 (s; 1H); 7.44 (q; J=7.7 Hz; 1H); 6.91-6.98 (m; 2H); 4.63 (s; 2H); 3.46-3.53 (m; 1H); 3.18 (s; 3H); 3.00-3.07 (m; 1H); 2.44-2.49 (m; 1H); 2.17-2.23 (m; 1H); 2.00-2.06 (m; 2H); 1.87-1.96 (m; 2H); 1.74-1.81 (m; 3H); 1.61-1.70 (m; 1H).

Example 5

Preparation of Compound 5 and Compound 6

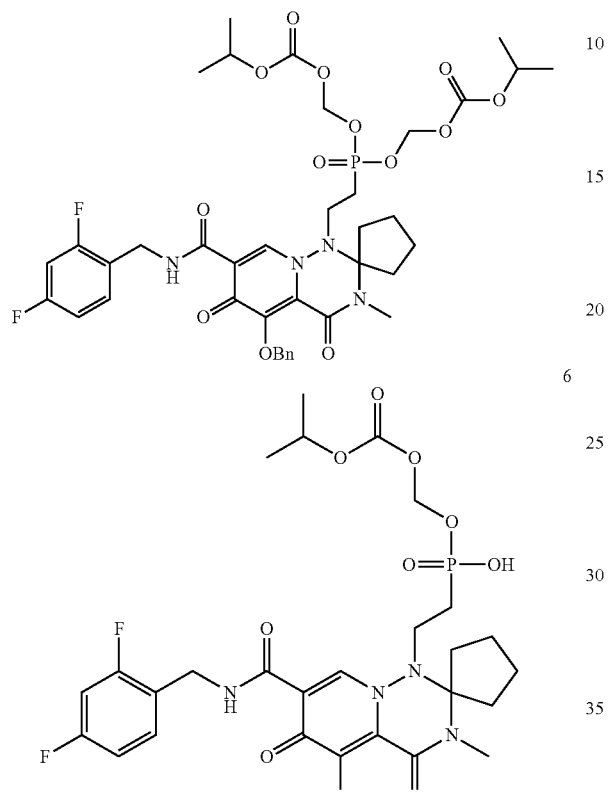

Compound 3 (250 mg, 0.405 mmol) and tetra-N-butylammonium iodide (74.9 mg, 0.203 mmol) in acetonitrile (2.0 mL) was treated at room temperature with N,N-diisopropylethylamine (0.354 ml, 2.027 mmol) and chloromethyl isopropyl carbonate (0.272 ml, 2.027 mmol). The reaction mixture was heated at 80° C. for 10 hours, cooled to room temperature, neutralized with glacial AcOH and directly purified using RP-HPLC to provide the separated compound 5 and compound 6.

Intermediate Compound 5: Mass (calculated) for $C_{39}H_{47}F_2N_4O_{13}P$: 848.3 found 849.5 (M+H)$^+$; $^1$H NMR (500 MHz, CDCl$_3$): δ 10.47 (s; 1H); 8.47 (s; 1H); 7.52 (d; J=7.3 Hz; 2H); 7.40 (q; J=7.7 Hz; 1H); 7.29-7.33 (m; 3H); 6.80-6.87 (m; 2H); 5.60-5.74 (m; 4H); 5.51 (d; J=10.3 Hz; 1H); 5.25 (d; J=10.3 Hz; 1H); 4.89-4.95 (m; 2H); 4.65 (d; J=5.4 Hz; 2H); 3.34-3.40 (m; 1H); 3.09 (s; 3H); 2.95-3.03 (m; 1H); 2.25-2.29 (m; 1H); 2.12-2.20 (m; 1H); 1.95-2.07 (m; 3H); 1.76-1.83 (m; 1H); 1.65-1.70 (m; 1H); 1.55-1.63 (m; 2H); 1.32 (d; J=6.2 Hz; 12H); 1.19-1.27 (m; 1H).

Intermediate Compound 6: Mass (calculated) for $C_{34}H_{39}F_2N_4O_{10}P$: 732.2 found 733.4 (M+H)$^+$; $^1$H NMR (500 MHz, CDCl$_3$): δ 10.64 (br s; 1H); 8.77 (s; 1H); 7.39-7.39 (m; 1H); 7.28 (d; J=8.9 Hz; 5H); 6.83-6.89 (m; 2H); 5.61 (d; J=12.7 Hz; 2H); 5.44 (d; J=10.7 Hz; 1H); 5.27 (d; J=10.7 Hz; 1H); 4.84-4.89 (m; 1H); 4.65 (s; 2H); 4.13-4.18 (m; 1H); 3.40 (br s; 1H); 3.08 (s; 3H); 2.98 (br s; 1H); 2.24 (br s; 1H); 1.97-2.13 (m; 4H); 1.80 (br s; 1H); 1.67 (t; J=9.6 Hz; 1H); 1.46-1.58 (m; 2H); 1.25-1.30 (m; 6H); 0.98-1.01 (m; 1H).

Example 6

Preparation of Compound 7

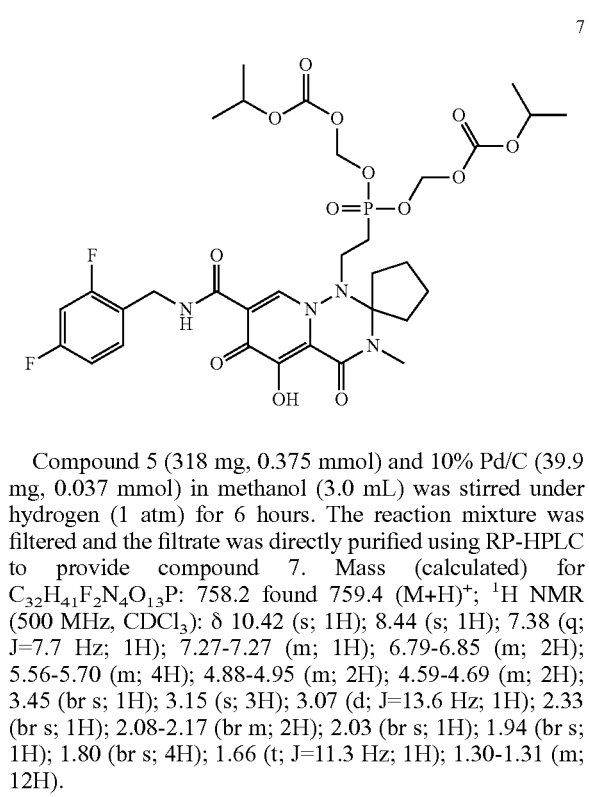

Compound 5 (318 mg, 0.375 mmol) and 10% Pd/C (39.9 mg, 0.037 mmol) in methanol (3.0 mL) was stirred under hydrogen (1 atm) for 6 hours. The reaction mixture was filtered and the filtrate was directly purified using RP-HPLC to provide compound 7. Mass (calculated) for $C_{32}H_{41}F_2N_4O_{13}P$: 758.2 found 759.4 (M+H)$^+$; $^1$H NMR (500 MHz, CDCl$_3$): δ 10.42 (s; 1H); 8.44 (s; 1H); 7.38 (q; J=7.7 Hz; 1H); 7.27-7.27 (m; 1H); 6.79-6.85 (m; 2H); 5.56-5.70 (m; 4H); 4.88-4.95 (m; 2H); 4.59-4.69 (m; 2H); 3.45 (br s; 1H); 3.15 (s; 3H); 3.07 (d; J=13.6 Hz; 1H); 2.33 (br s; 1H); 2.08-2.17 (br m; 2H); 2.03 (br s; 1H); 1.94 (br s; 1H); 1.80 (br s; 4H); 1.66 (t; J=11.3 Hz; 1H); 1.30-1.31 (m; 12H).

Example 7

Preparation of Compound 8

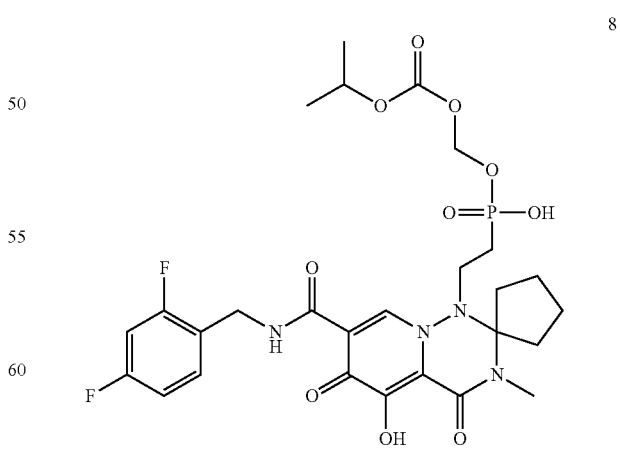

Compound 6 (34 mg, 0.046 mmol) and Pd/C (24.69 mg, 0.023 mmol) in methanol (3.0 mL) was stirred under hydrogen (1 atm) for 6 hours. The reaction mixture was filtered and the filtrate was directly purified using RP-HPLC to provide compound 8. Mass (calculated) for $C_{27}H_{33}F_2N_4O_{10}P$: 642.2 found 643.4 (M+H)+; 1H NMR (500 MHz, CDCl3): δ 10.50 (s; 1H); 8.62 (s; 1H); 7.34-7.39 (m; 1H); 6.79-6.85 (m; 2H); 5.62 (d; J=12.5 Hz; 2H); 4.86-4.90 (m; 1H); 4.56-4.68 (m; 2H); 3.43-3.52 (br m; 1H); 3.14 (s; 3H); 3.03-3.08 (m; 1H); 2.31-2.36 (m; 1H); 2.13-2.19 (m; 1H); 2.02-2.07 (m; 2H); 1.92-1.95 (m; 2H); 1.76-1.83 (br m; 3H); 1.63-1.67 (m; 1H); 1.29 (d; J=6.3 Hz; 6H).

Example 8

Preparation of Compound 9

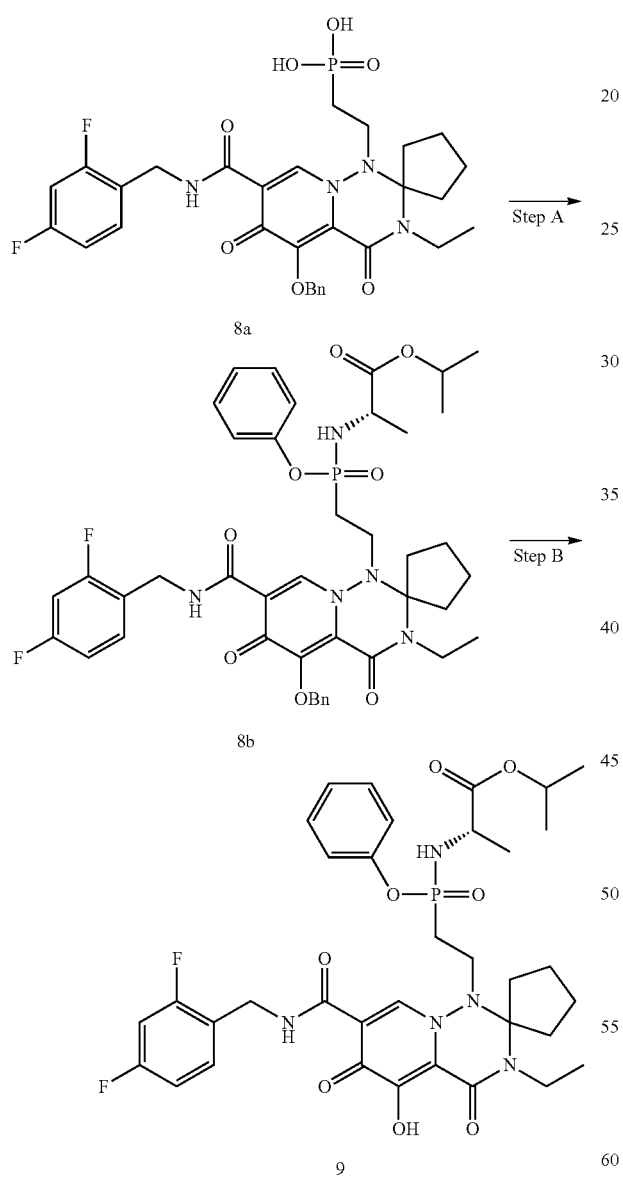

Step A—Synthesis of Compound 8b

A mixture of compound 8a (prepared in a similar manner to compound 3) (40 mg, 0.063 mmol), alanine isopropyl ester hydrochloride (19.14 mg, 0.114 mmol) and phenol (23.88 mg, 0.254 mmol) in pyridine (300 μl) was warmed to 60° C. Separately, a solution of 2,2'-dipyridyl disulfide (84 mg, 0.381 mmol), triphenylphosphine (100 mg, 0.381 mmol) and triethylamine (106 μl, 0.761 mmol) in pyridine (600 μl) was prepared. This solution was added to the pre-heated mixture and the mixture was allowed to stir at 60° C. under nitrogen for 2 hours. The reaction mixture was concentrated in vacuo and the resulting residue was purified using column chromatography on silica gel (0%-100% EtOAc/hexanes) to provide compound 8b. Mass (calculated) for $C_{42}H_{48}F_2N_5O_8P$: 819.3 found 820.2 (M+H)+;

Step B—Synthesis of Compound 9

A mixture of compound 8b (40 mg, 0.049 mmol) and Pd/C (5.19 mg, 4.88 μmol) in methanol (2 mL) was stirred under hydrogen (1 atm) for 14 hours. The reaction mixture was filtered and the filtrate was directly purified using RP-HPLC (acetonitrile/water with 0.1% NH4HCO3 buffer) to provide compound 9. Mass (calculated) for $C_{35}H_{42}P_2N_5O_8P$: 729.3 found 730.3 (M+H)+;

Example 9

Preparation of Intermediate Compound 10

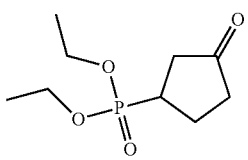

A 250 mL glass pressure vessel was charged with phenol (25 mL), triethylphosphite (21.86 ml, 0.125 mol) and cyclopent-2-enone (8.38 ml, 0.1 mol). The reaction mixture was sealed and heated at 100° C. for 24 hours, cooled to room temperature and transferred to a separatory funnel with ethyl acetate (250 mL). The resulting mixture was washed with 2M aqueous potassium carbonate (4×125 mL), dried over anhydrous sodium sulfate, filtered and the filtrate was concentrated in vacuo. Purification by column chromatography on silica gel by eluting with 100% ethyl acetate provided the ethyl phenyl ether byproduct followed by elution with 20% MeOH/EtOAc provided intermediate compound 10. TLC (silica gel, 100% ethyl acetate) Rf 0.2; Mass (calculated) for $C_9H_{17}O_4P$: 220.1 found 221.0 (M+H)+; 1H NMR (500 MHz, CDCl3): δ 4.09-4.18 (m; 4H); 2.37-2.53 (m; 4H); 2.11-2.31 (m; 3H); 1.34 (td; J=7.1; 2.1 Hz; 6H)\

Example 10

Preparation of Intermediate Compound 11 and Intermediate Compound 12

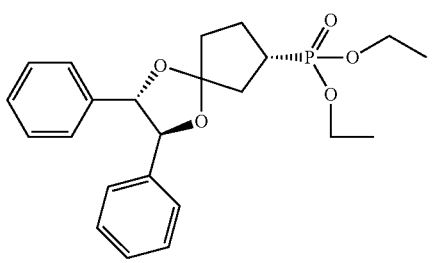

diastereomer A (2S, 3S, 7S)

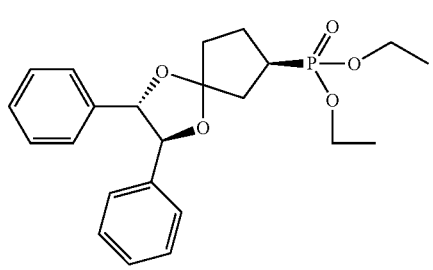

diastereomer B (2S, 3S, 7R)

A mixture of intermediate compound 10 (15 g, 68.1 mmol), (S,S)-(–)-hydrobenzoin (21.89 g, 102 mmol) and p-toluenesulfonic acid monohydrate (1.296 g, 6.81 mmol) in toluene (100.0 mL) was heated at 90° C. for 16 hours, cooled to room temperature and directly purified using column chromatography on silica gel (0 to 100% EtOAc/hexanes; eluted after the hydrobenzoin) provided products as a mixture of diastereomers. Mass (calculated) for $C_{23}H_{29}O_5P$: 416.2 found 417.5 (M+H)$^+$. The diastereomers were separated by preparative SFC (2.1×25.0 cm, (S,S)-Whelk-O 1 Regis Technologies, 20% isopropanol in SC—CO$_2$ at 100 g/min, 140 bar, 25° C.) to provide compound 11, diastereomer A (2S,3S,7S) and compound 12, diastereomer B (2S,3S,7R).

Intermediate Compound 11: $^1$H NMR (500 MHz, CDCl$_3$): δ 7.31-7.32 (m; 6H); 7.20-7.24 (m; 4H); 4.71 (d; J=8.6 Hz; 1H); 4.67 (d; J=8.6 Hz; 1H); 4.14-4.16 (m; 4H); 1.99-2.46 (m; 7H); 1.35 (t; J=7.1 Hz; 6H).

Intermediate Compound 12: $^1$H NMR (500 MHz, CDCl$_3$): δ 7.32-7.33 (m; 6H); 7.21-7.27 (m; 4H); 4.75 (d; J=8.6 Hz; 1H); 4.72 (d; J=8.6 Hz; 1H); 4.11-4.19 (m; 4H); 2.51-2.58 (m; 1H); 2.38-2.44 (m; 1H); 2.28-2.34 (m; 2H); 2.07-2.12 (m; 3H); 1.34 (t; J=7.1 Hz; 6H).

Absolute stereochemistry was assigned using vibrational circular dichroism (VCD).

The observed VCD spectrum of Diastereomer A compares better with the Boltzmann population-weighted calculated spectrum (labeled as Final) of the (2S,3S,7S) configuration for the monomer over the range 1000-1850 cm$^{-1}$.

The observed VCD spectrum of Diastereomer B compares better with the Boltzmann population-weighted calculated spectrum (labeled as Final) of the (2S,3S,7R) configuration for the monomer over the range 1000-1850 cm$^{-1}$.

Example 11

Preparation of Intermediate Compound 13

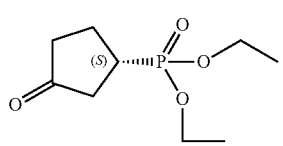

13

Intermediate ompound 11 (2.00 g, 4.80 mmol) and Pd/C (10 wt %, 0.5 g, 0.470 mmol) in methanol (20 mL) was allowed to stir at room temperature under hydrogen gas (1 atm) for 48 hours. The reaction mixture was filtered and the filtrate was concentrated in vacuo to provide intermediate compound 13 that was used without further purification. Mass (calculated) for $C_9H_{17}O_4P$: 220.1 found 221.1 (M+H)$^+$; $^1$H NMR (500 MHz, CDCl$_3$): δ 4.09-4.18 (m; 4H); 2.37-2.53 (m; 4H); 2.11-2.31 (m; 3H); 1.34 (td; J=7.1; 2.1 Hz; 6H)

Example 12

Preparation of Intermediate Compound 14

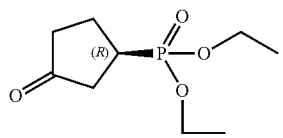

14

Intermediate ompound 12 (2.00 g, 4.80 mmol) and Pd/C (10 wt %, 0.5 g, 0.470 mmol) in methanol (20 mL) was allowed to stir at room temperature under hydrogen gas (1 atm) for 48 hours. The reaction mixture was filtered and the filtrate was concentrated in vacuo to provide intermediate compound 14 that was used without further purification. Mass (calculated) for $C_9H_{17}O_4P$: 220.1 found 221.1 (M+H)$^+$; $^1$H NMR (500 MHz, CDCl$_3$): δ 4.09-4.18 (m; 4H); 2.37-2.53 (m; 4H); 2.11-2.31 (m; 3H); 1.34 (td; J=7.1; 2.1 Hz; 6H)

Example 13

Preparation of Intermediate Compound 15 and Intermediate Compound 16

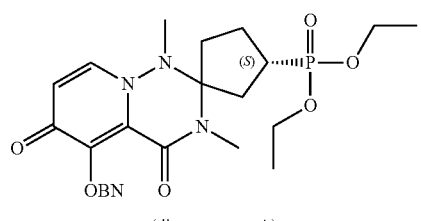

(diastereomer A)

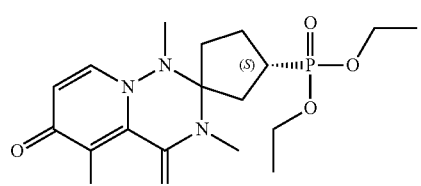

(diastereomer B)

Intermediate compound 1c (1.312 g, 4.80 mmol) and intermediate compound 13 (1.057 g, 4.80 mmol) in 1,4-dioxane (8.0 mL) was treated at room temperature with trifluoroacetic acid (0.370 ml, 4.80 mmol). The reaction mixture was heated at 50° C. for 16 hours, cooled to room temperature and directly loaded onto a silica gel column. Purification by column chromatography on silica gel (0 to 30% MeOH/dichloromethane) provided the hydrazone intermediate that was used without further purification. The hydrazone intermediate was taken up in dimethylsulfoxide (8 mL) and treated with iodomethane (0.600 ml, 9.60 mmol), tetrabutylammonium hydroxide triacontahydrate (0.384 g, 0.480 mmol) and finely-powdered potassium hydroxide (0.539 g, 9.60 mmol). The reaction mixture was allowed to stir at room temperature for 6 hours, neutralized with glacial acetic acid and directly purified using RP-HPLC to provide the products as a mixture of diastereomers. The diastereomers were separated by chiral SFC (OZ—H (2×25 cm), 30% methanol in SC—$CO_2$, 100 bar, 60 mL/min, 220 nm) to provide Intermediate Compound 15, diastereomer A (earlier eluting) and Intermediate Compound 16, diastereomer B (later eluting).

Intermediate Compound 15, diastereomer A: Mass (calculated) for $C_{24}H_{32}N_3O_6P$: 489.2 found 490.0 (M+H)$^+$; $^1$H NMR (500 MHz, CDCl$_3$): δ 7.53-7.56 (m; 2H); 7.25-7.35 (m; 4H); 6.51 (br s; 1H); 5.52-5.56 (m; 1H); 5.20-5.23 (m; 1H); 4.06-4.15 (m; 4H); {3.12 (s; 3H); 3.08 (s; 3H)}; 2.72 (s; 3H); 2.25-2.38 (m; 1H); 2.07 (br s; 1H); 1.89-1.97 (br m; 3H); 1.64-1.72 (m; 1H); 1.42-1.47 (m; 1H); 1.28-1.35 (m; 6H).

Intermediate Compound 16, diastereomer B: Mass (calculated) for $C_{24}H_{32}N_3O_6P$: 489.2 found 490.3 (M+H)$^+$; $^1$H NMR (500 MHz, CDCl$_3$): δ 7.54-7.62 (m; 2H); 7.26-7.33 (m; 4H); 6.61-6.67 (br m; 1H); 5.57 (t; J=10.9 Hz; 1H); 5.21 (t; J=8.4 Hz; 1H); 4.01-4.14 (br m; 4H); {3.13 (s; 3H); 3.11 (s; 3H)}; 2.73 (s; 3H); 2.43 (br s; 1H); 2.14-2.33 (br m; 3H); 1.79-1.95 (br m; 2H); 1.64-1.68 (m; 1H); 1.25-1.37 (m; 6H).

Example 14

Preparation of Intermediate Compound 17 and Intermediate Compound 18

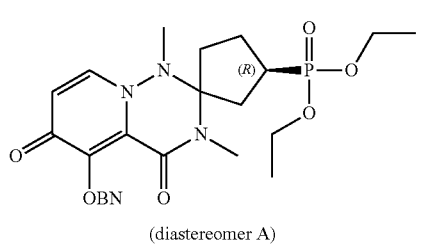

17

(diastereomer A)

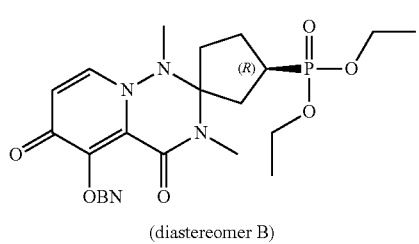

18

(diastereomer B)

Intermediate compound 1c (1.312 g, 4.80 mmol) and intermediate compound 14 (1.057 g, 4.80 mmol) in 1,4-dioxane (8.0 mL) was treated at room temperature with trifluoroacetic acid (0.370 ml, 4.80 mmol). The reaction mixture was heated at 50° C. for 16 hours, cooled to room temperature and directly loaded onto a silica gel column. Purification by column chromatography on silica gel (0 to 30% MeOH/dichloromethane) provided the hydrazone intermediate that was used without further purification. The hydrazone intermediate was taken up in dimethylsulfoxide (8 mL) and treated with iodomethane (0.600 ml, 9.60 mmol), tetrabutylammonium hydroxide triacontahydrate (0.384 g, 0.480 mmol) and finely-powdered potassium hydroxide (0.539 g, 9.60 mmol). The reaction mixture was allowed to stir at room temperature for 6 hours, neutralized with glacial acetic acid and directly purified using RP-HPLC to provide the products as a mixture of diastereomers. The diastereomers were separated by chiral SFC (OZ—H (2×25 cm), 45% methanol in SC—$CO_2$, 100 bar, 50 mL/min, 220 nm) to provide Intermediate Compound 17, diastereomer A and Intermediate Compound 18, diastereomer B.

Intermediate Compound 17, diastereomer A: Mass (calculated) for $C_{24}H_{32}N_3O_6P$: 489.2 found 490.3; $^1$H NMR (500 MHz, CDCl$_3$): δ 7.61 (d; J=7.1 Hz; 2H); 7.54 (s; 4H); 6.47 (br s; 1H); 5.54-5.58 (m; 1H); 5.18-5.22 (m; 1H); 4.01-4.15 (m; 4H); {3.12 (s; 3H); 3.10 (s; 3H)}; 2.71 (s; 3H); 2.42 (br s; 1H); 2.12-2.29 (br m; 3H); 1.82-1.91 (br m; 3H); 1.25-1.37 (m; 6H).

Intermediate Compound 18, diastereomer B: Mass (calculated) for $C_{24}H_{32}N_3O_6P$: 489.2 found 490.3.

$^1$H NMR (500 MHz, CDCl$_3$): δ 7.53-7.56 (m; 2H); 7.37 (br s; 1H); 7.25-7.31 (m; 3H); 6.55 (br s; 1H); 5.52-5.56 (m; 1H); 5.21-5.23 (m; 1H); {4.09-4.15 (br m; 4H); 3.72 (q; J=7.0 Hz; 4H)}; {3.12 (s; 3H); 3.08 (s; 3H)}; 2.73 (s; 3H); 2.18-2.44 (br m; 3H); 1.90-2.06 (br m; 3H); 1.42-1.45 (br m; 1H); 1.23-1.37 (m; 6H).

Example 15

Preparation of Intermediate Compound 19

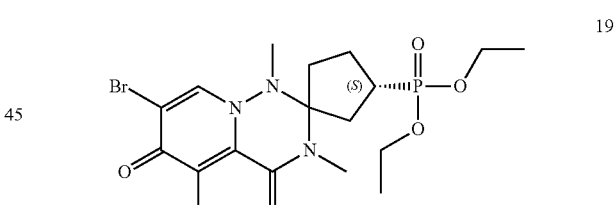

19

Intermediate Compound 15, diastereomer A (709 mg, 1.448 mmol) in N,N-dimethylformamide (3 mL) was treated at room temperature with N-bromosuccinimide (516 mg, 2.90 mmol). The reaction mixture was allowed to stir at room temperature for 4 hours, diluted with acetonitrile and directly purified using RP-HPLC to provide intermediate compound 19. Mass (calculated) for $C_{24}H_{31}BrN_3O_6P$: 567.1, 569.1 found 568.4, 570.2 (M+H)$^+$; $^1$H NMR (500 MHz, CDCl$_3$): δ 7.80-7.82 (m; 1H); 7.54-7.57 (m; 2H); 7.27-7.31 (m; 3H); 5.51-5.54 (m; 1H); 5.18-5.21 (m; 1H); 4.07-4.18 (m; 4H); {3.13 (s; 3H); 3.08 (s; 3H)}; 2.76 (s; 3H); 2.26-2.49 (m; 2H); 2.18-2.21 (m; 1H); 2.04-2.12 (m; 1H); 1.89-1.99 (m; 1H); 1.68-1.73 (m; 1H); 1.44-1.54 (m; 1H); 1.29-1.36 (m; 6H).

Example 16

Preparation of Compound 20 and Compound 21

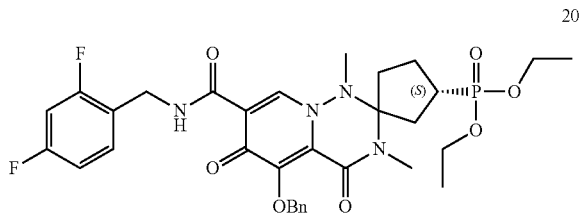

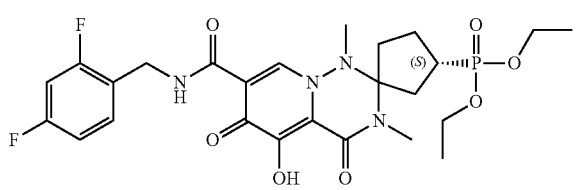

Intermediate compound 19 (715 mg, 1.258 mmol) in DMSO (4.0 mL) was sub-surface sparged with nitrogen for 10 minutes at room temperature and treated with 2,4-difluorophenylmethanamine (0.329 ml, 2.77 mmol), N,N-diisopropylethylamine (0.439 ml, 2.52 mmol) and Pd(Ph$_3$P)$_4$ (291 mg, 0.252 mmol). The reaction mixture was heated at 90° C. for 8 hours under carbon monoxide (1 atm), cooled to room temperature and filtered. The filtrate was neutralized with glacial acetic acid and directly purified using RP-HPLC to provide compound 20 and compound 21.

Compound 20: Mass (calculated) for $C_{32}H_{37}F_2N_4O_7P$: 658.2 found 659.4 (M+H)$^+$; $^1$H NMR (500 MHz, CDCl$_3$): δ 10.48 (br s; 1H); 8.47 (s; 1H); 7.52-7.55 (m; 2H); 7.38-7.41 (m; 1H); 7.27-7.35 (m; 3H); 6.80-6.87 (m; 2H); 5.47-5.51 (m; 1H); 5.23 (d; J=10.2 Hz; 1H); 4.64-4.65 (m; 2H); 4.05-4.15 (m; 4H); {3.14 (s; 3H); 3.10 (s; 3H)}; 2.77 (s; 3H); 2.28-2.48 (m; 2 F); 2.20-2.22 (m; 1H); 2.05-2.13 (m; 1H); 1.89-2.01 (m; 1H); 1.68-1.78 (m; 1H); 1.42-1.55 (m; 1H); 1.27-1.36 (m; 6H).

Compound 21: Mass (calculated) for $C_{25}H_{31}F_2N_4O_7P$: 568.2 found 569.6 (M+H)$^+$; $^1$H NMR (500 MHz, CDCl$_3$): δ 10.45 (s; 1H); 8.47 (s; 1H); 7.34-7.39 (m; 1H); 6.79-6.85 (m; 2H); 4.65 (s; 2H); 4.09-4.20 (m; 4H); {3.19 (s; 3H); 3.16 (s; 3H)}; {2.81 (s; 3H); 2.80 (s; 3H)}; 2.36-2.51 (m; 2H); 2.27-2.30 (m; 1H); 2.13-2.19 (m; 2H); 1.92-2.01 (m; 1H); 1.85 (t; J=7.7 Hz; 1H); 1.29-1.39 (m; 6H).

Example 17

Preparation of Compound 22

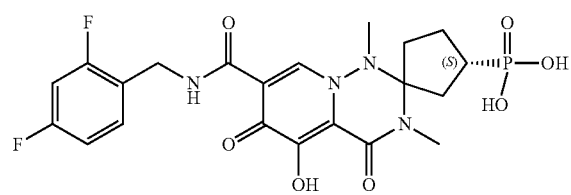

Compound 21(110 mg, 0.193 mmol) in acetonitrile (1.5 mL) was treated at room temperature with 2,6-lutidine (0.169 mL, 1.451 mmol) and TMS-Br (0.176 mL, 1.354 mmol). The reaction mixture was allowed to stir at 50° C. for 2 hours, cooled to 0° C., quenched with water (3 mL) and allowed to stir for 1 hour while warming to room temperature. The reaction mixture was directly purified using RP-HPLC to provide compound 22. Mass (calculated) for $C_{21}H_{23}F_2N_4O_7P$: 512.1 found 513.3 (M+H)$^+$; $^1$H NMR (400 MHz, DMSO): δ 10.29 (t; J=5.8 Hz; 1H); 8.30-8.31 (m; 1H); 7.40 (q; J=7.9 Hz; 1H); 7.23 (t; J=10.0 Hz; 1H); 7.05 (t; J=8.6 Hz; 1H); 4.50-4.53 (m; 2H); {3.10 (s; 3H); 3.05 (s; 3H)}; 2.74 (s; 3H); 2.19-2.32 (m; 2H); 2.03-2.10 (m; 1H); 1.84-2.00 (m; 2H); 1.70-1.82 (m; 2H).

Example 18

Preparation of Compound 23

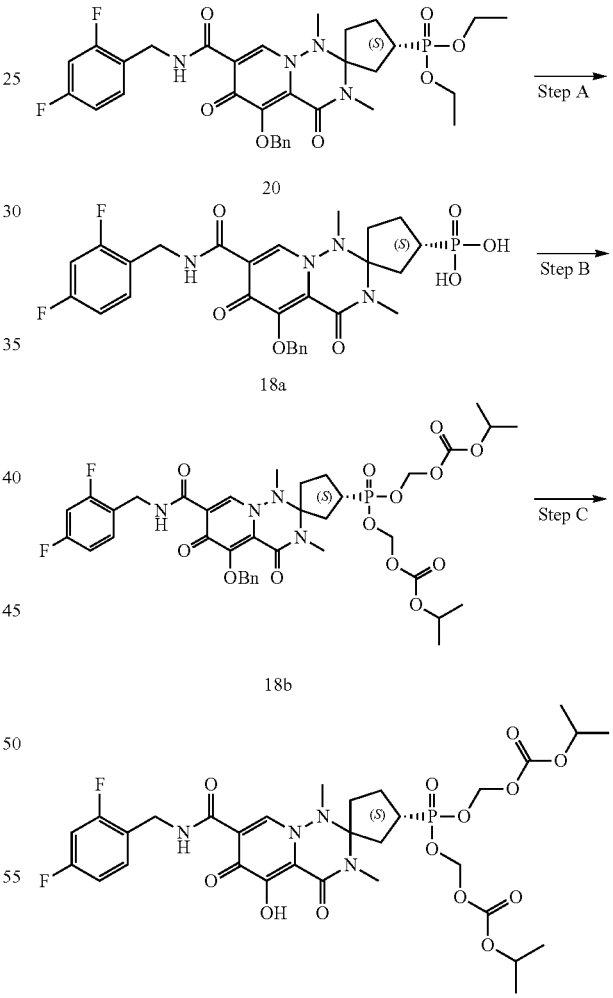

Step A—Synthesis of Intermediate Compound 18a

Compound 20 (504 mg, 0.765 mmol) in acetonitrile (7 mL) was treated at room temperature with 2,6-lutidine (0.668 mL, 5.74 mmol) and trimethylsilyl bromide (0.695 mL, 5.36 mmol). The reaction mixture was allowed to stir at 50° C. for 2 hours, cooled to 0° C., quenched with water (7 mL) and allowed to stir for 1 hour while warming to room temperature. The reaction mixture was directly purified using RP-HPLC to provide Intermediate Compound 18a. Mass (calculated) for $C_{28}H_{29}P_2N_4O_7P$: 602.2 found 603.4 (M+H)$^+$.

Step B—Synthesis of Compound 18b

Intermediate compound 18a (460 mg, 0.763 mmol) in acetonitrile (7 mL) was treated with N,N-diisopropylethylamine (1.333 mL, 7.63 mmol), tetra-N-butylammonium bromide (246 mg, 0.763 mmol) and chloromethyl isopropyl carbonate (0.810 mL, 6.11 mmol). The suspension was warmed to 60° C., allowed to stir for 2 days at 60° C., cooled to room temperature and concentrated in vacuo. The resulting residue was purified using column chromatography on silica gel (0 to 100% (25% EtOH+EtOAc)/hexanes) to provide compound 18b. Mass (calculated) for $C_{38}H_{45}F_2N_4O_{13}P$: 834.3 found 835.4 (M+H)$^+$.

Step C—Synthesis of Compound 23

Compound 18b (529 mg, 0.634 mmol) and Pd/C (10 wt %, 67.4 mg, 0.063 mmol) in methanol (6 mL) was stirred under hydrogen (1 atm) for 16 hours. Dichloromethane (30 mL) was added to the reaction mixture to dissolve the resulting precipitate and the mixture was filtered. The filtrate was concentrated in vacuo and the resulting residue was purified using RP-HPLC to provide compound 23. Mass (calculated) for $C_{31}H_{39}F_2N_4O_{13}P$: 744.2 found 745.3 (M+H)$^+$; $^1$H NMR (400 MHz, DMSO): δ 10.29 (t; J=6.0 Hz; 1H); {8.37 (s; 1H); 8.31 (s; 1H)}; 7.40 (q; J=7.8 Hz; 1H); 7.23 (t; J=10.0 Hz; 1H); 7.05 (t; J=8.4 Hz; 1H); 5.51-5.63 (m; 4H); 4.69-4.82 (m; 2H); 4.52 (s; 2H); {3.09 (s; 3H); 3.04 (s; 3H)}; 2.74 (s; 3H); 2.14-2.36 (m; 2H); 1.72-2.00 (br m; 5H); 1.14-1.23 (m; 12H).

Example 19

Preparation of Compound 24

Compound 24 was prepared from intermediate compound 16 (diastereomer B) using the methods described in Examples 15 and 16. Mass (calculated) for $C_{25}H_{31}P_2N_4O_7P$: 568.2 found 569.6 (M+H)$^+$; $^1$H NMR (500 MHz, CDCl$_3$): δ 10.43 (s; 1H); 8.51-8.54 (m; 1H); 7.37 (q; J=7.7 Hz; 1H); 6.79-6.85 (m; 2H); 4.65 (s; 2H); 4.10-4.23 (m; 4H); {3.21 (s; 3H); 3.17 (s; 3H)}; {2.81 (s; 3H); 2.78 (s; 3H)}; 2.43-2.53 (m; 2H); 2.17-2.33 (m; 2H); 1.91-2.06 (m; 2H); 1.71-1.77 (m; 1H); 1.30-1.40 (m; 6H).

Example 20

Preparation of Compound 25

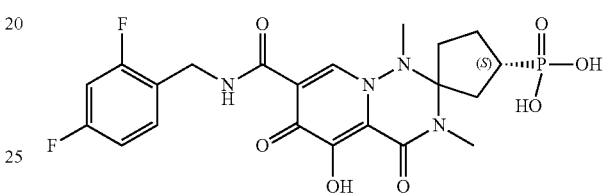

Compound 25 was prepared from compound 24 using the methods described in Example 17. Mass (calculated) for $C_{11}H_{23}F_2N_4O_7P$: 512.1 found 513.3 (M+H)$^+$; $^1$H NMR (400 MHz, DMSO): δ 10.27-10.31 (m; 1H); {8.35 (d; J=1.6 Hz; 1H); 8.32 (d; J=1.6 Hz; 1H)}; 7.40 (q; J=8.0 Hz; 1H); 7.23 (t; J=10.0 Hz; 1H); 7.05 (t; J=8.6 Hz; 1H); 4.52 (d; J=5.7 Hz; 2H); 3.11 (s; 3H); {2.73 (s; 3H); 2.71 (s; 3H)}; 2.52-2.57 (m; 1H); 2.26-2.42 (m; 2H); 1.90-2.12 (m; 3H); 1.74-1.85 (m; 1H).

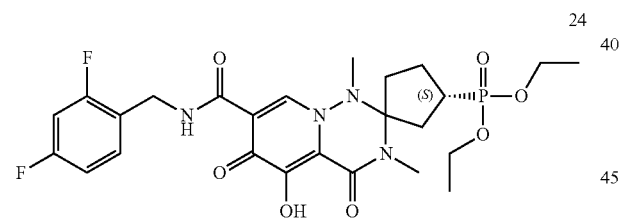

Example 21

Preparation of Compound 26

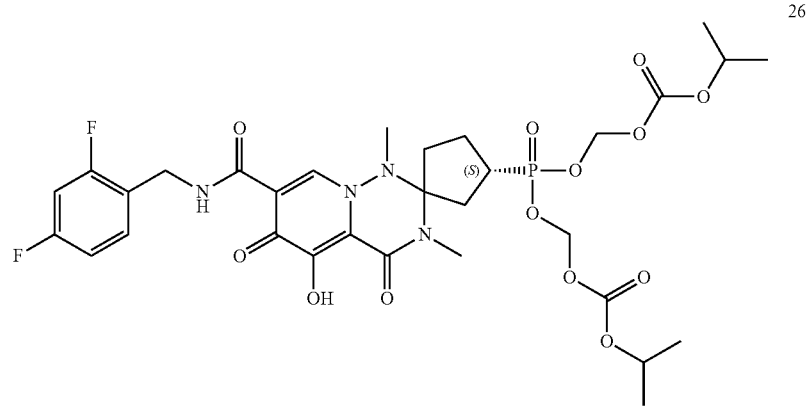

Compound 26 was prepared from intermediate compound 16 (diastereomer B) using the methods described in Examples 15, 16 and 18. Mass (calculated) for $C_{31}H_{39}P_2N_4O_{13}P$: 744.2 found 745.3 (M+H)$^+$; $^1$H NMR (400 MHz, DMSO): δ 10.24-10.27 (m; 1H); {8.43 (s; 1H); 8.25 (s; 1H)}; 7.35-7.42 (m; 1H); 7.23 (t; J=10.0 Hz; 1H); 7.01-7.07 (m; 1H); 5.48-5.64 (m; 4H); 4.71-4.85 (m; 2H); 4.52 (s; 2H); {3.10 (s; 3H); 3.09 (s; 3H)}; 2.83-2.97 (br m; 1H); {2.74 (s; 3H); 2.71 (s; 3H)}; 2.60-2.66 (m; 1H); 2.17-2.40 (m; 1H); 1.83-2.09 (m; 4H); 1.14-1.24 (m; 12H).

Example 22

Preparation of Compound 27

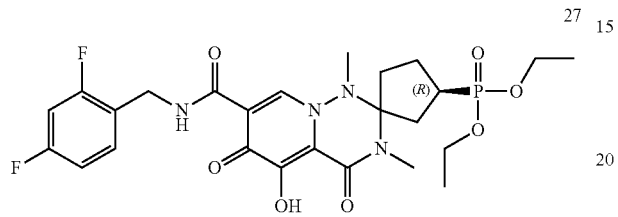

Compound 27 was prepared from intermediate compound 17 (diastereomer A) using the methods described in Examples 15 and 16. Mass (calculated) for $C_{25}H_{31}P_2N_4O_7P$: 568.2 found 569.4 (M+H)$^+$; $^1$H NMR (500 MHz, CDCl$_3$): δ 10.41 (s; 1H); {8.52 (s; 1H); 8.49 (s; 1H);} 7.37 (q; J=7.8 Hz; 1H); 6.78-6.84 (m; 2H); 4.65 (s; 2H); 4.10-4.22 (m; 4H); {3.21 (s; 3H); 3.17 (s; 3H)}; {2.81 (s; 3H); 2.78 (s; 3H)}; 2.44-2.55 (m; 2H); 2.15-2.31 (m; 3H); 2.02-2.08 (m; 1H); {1.92-1.99 (m; 1H); 1.71-1.77 (m; 1H)}; 1.30-1.40 (m; 6H).

Example 23

Preparation of Compound 28

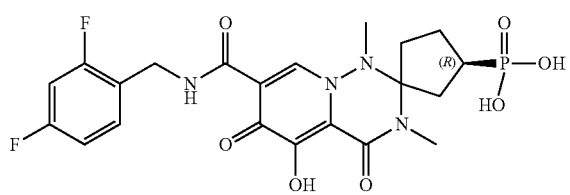

Compound 28 was prepared from compound 27 using the methods described in Example 17. Mass (calculated) for $C_{21}H_{23}P_2N_4O_7P$: 512.1 found 513.2 (M+H)$^+$; $^1$H NMR (400 MHz, DMSO): δ 10.29 (s; 1H); {8.35 (s; 1H); 8.32 (s; 1H)}; 7.40 (q; J=8.0 Hz; 1H); 7.23 (t; J=10.1 Hz; 1H); 7.05 (t; J=8.6 Hz; 1H); 4.52 (s; 2H); 3.11 (s; 3H); {2.73 (s; 3H); 2.71 (s; 3H)}; 2.27-2.38 (m; 2H); 2.10-2.17 (m; 1H); 1.91-2.04 (m; 3H); 1.73-1.83 (m; 1H).

Example 24

Preparation of Compound 29

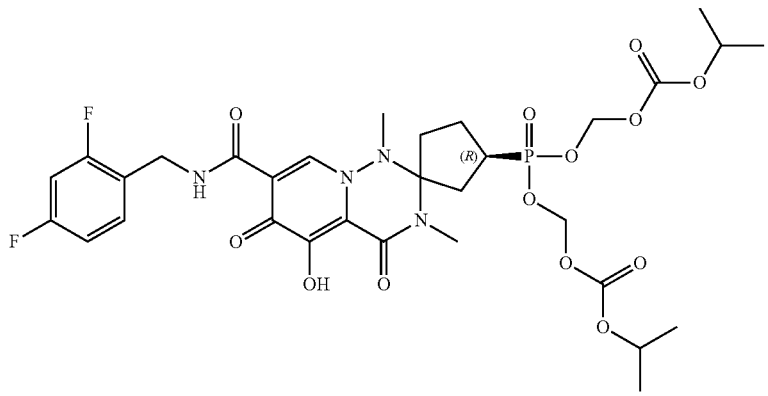

Compound 29 was prepared from compound 17 (diastereomer A) using the methods described in Examples 15, 16 and 18. Mass (calculated) for $C_{31}H_{39}P_2N_4O_{13}P$: 744.2 found 745.3 (M+H)$^+$;

Example 25

Preparation of Compound 30

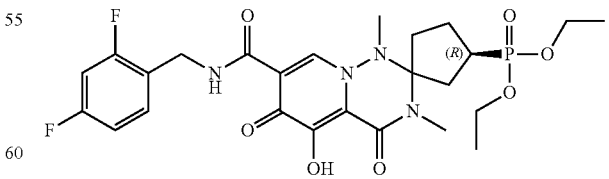

Compound 30 was prepared from compound 18 (diastereomer B) using the methods described in Examples 15 and 16. Mass (calculated) for $C_{25}H_{31}P_2N_4O_7P$: 568.2 found 569.3 (M+H)$^+$; $^1$H NMR (500 MHz, CDCl$_3$): δ 10.44 (br s; 1H); 8.46 (s; 1H); 7.37 (s; 1H); 6.79-6.84 (m; 2H); 4.64-4.65

(m; 2H); 4.07-4.20 (m; 4H); {3.19 (s; 3H); 3.16 (s; 3H)}; 2.80 (s; 3H); 2.39-2.56 (br m; 2H); 2.06-2.28 (br m; 3H); 1.87-2.03 (m; 2H); 1.29-1.39 (m; 6H).

Example 26

Preparation of Compound 31

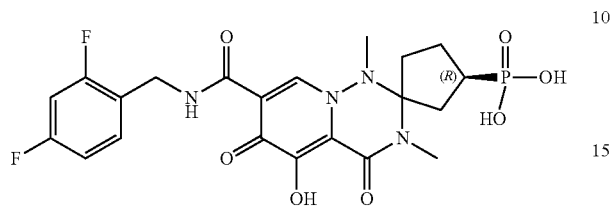

Compound 31 was prepared from compound 30 using the methods described in Example 17. Mass (calculated) for $C_{11}H_{23}F_2N_4O_7P$: 512.1 found 513.2 (M+H)$^+$; $^1$H NMR (400 MHz, DMSO): δ 10.29 (s; 1H); 8.31 (s; 1H); 7.40 (q; J=7.9 Hz; 1H); 7.23 (t; J=10.1 Hz; 1H); 7.05 (t; J=8.7 Hz; 1H); 4.52 (s; 2H); {3.10 (s; 3H); 3.05 (s; 3H)}; 2.74 (s; 3H); 2.22-2.29 (m; 2H); 2.05-2.11 (m; 1H); 1.85-1.99 (m; 2H); 1.70-1.81 (m; 2H).

Example 27

Preparation of Compound 32

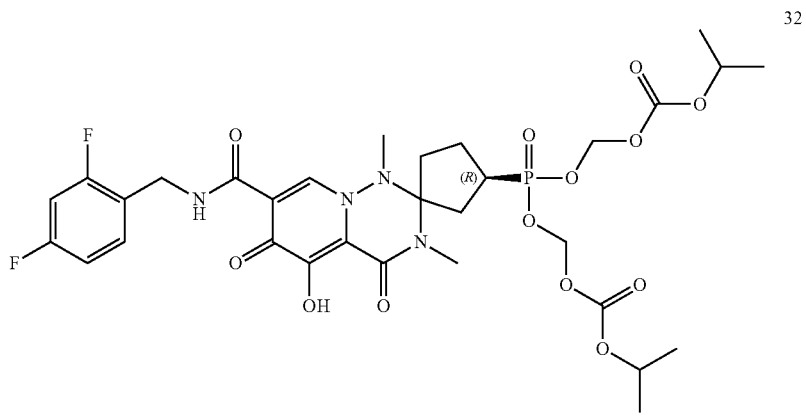

Compound 32 was prepared from intermediate compound 18 (diastereomer B) using the methods described in Examples 15, 16 and 18. Mass (calculated) for $C_{31}H_{39}F_2N_4O_{13}P$: 744.2 found 745.7 (M+H)$^+$; 1H NMR (400 MHz, DMSO): δ 10.26-10.30 (m; 1H); {8.37 (s; 1H); 8.31 (s; 1H)}; 7.40 (d; J=7.8 Hz; 1H); 7.20-7.26 (m; 1H); 7.05 (t; J=8.8 Hz; 1H); 5.50-5.64 (m; 4H); 4.73-4.85 (m; 2H); 4.52 (s; 2H); {3.09 (s; 3H); 3.04 (s; 3H)}; 2.74 (s; 3H); 2.09-2.32 (m; 3H); 1.74-2.08 (m; 4H); 1.14-1.24 (m; 12H).

The following compounds of the present invention were made using the methodology described examples 1-18 and substituting the appropriate reactants and/or reagents:

| Compound | Structure | Stereochemistry | Exact Mass [M + H]+ |
|---|---|---|---|
| 33 | 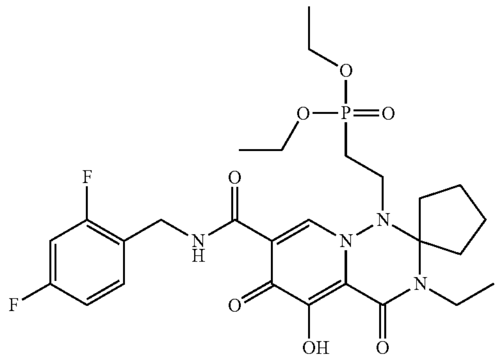 [SMILES: CCOP(=O)(CCN1n2cc(C(=O)NCc3ccc(F)cc3F)c(=O)c(O)c2C(=O)N(CC)C12CCCC2)OCC] | n/a | (calculated) 597.2, found 597.1 |
| 34 | 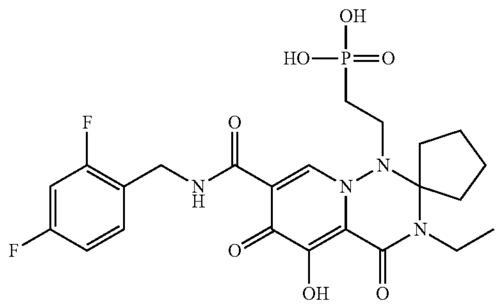 [SMILES: CCN1C(=O)c2c(O)c(=O)c(C(=O)NCc3ccc(F)cc3F)cn2N(CCP(=O)(O)O)C12CCCC2] | n/a | (calculated) 541.2, found 540.8 |
| 35 | 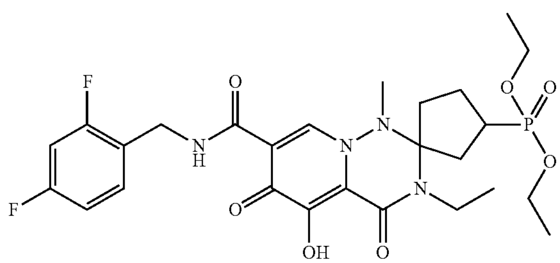 [SMILES: CCOP(=O)(OCC)C1CCC2(C1)N(CC)C(=O)c1c(O)c(=O)c(C(=O)NCc3ccc(F)cc3F)cn1N2C] | mixture of diastereomers | (calculated) 583.2, found 583.2 |
| 36 | 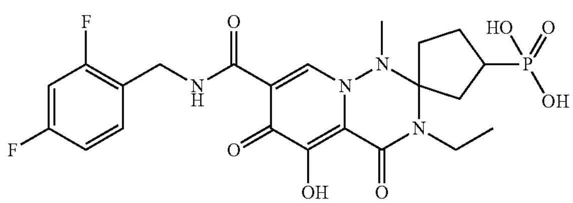 [SMILES: CCN1C(=O)c2c(O)c(=O)c(C(=O)NCc3ccc(F)cc3F)cn2N(C)C12CCC(P(=O)(O)O)C2] | mixture of diastereomers | (calculated) 527.2, found 527.5 |
| 37 | 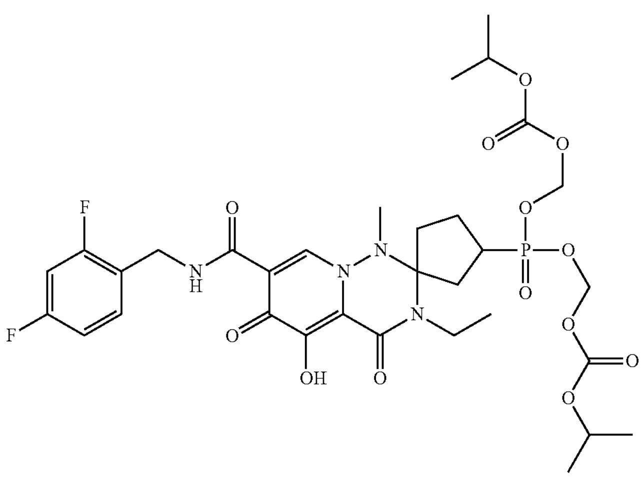 [SMILES: CCN1C(=O)c2c(O)c(=O)c(C(=O)NCc3ccc(F)cc3F)cn2N(C)C12CCC(P(=O)(OCOC(=O)OC(C)C)OCOC(=O)OC(C)C)C2] | mixture of diasteromers | (calculated) 759.2, found 759.3 |

Example 28

Assessing Antiviral Potency Using An HIV-1 Infection Assay

HIV-1 replication was monitored using MT4-gag-GFP clone D3 (hereafter designate MT4-GFP), which are MT-4 cells modified to harbor a GFP reporter gene, the expression of which is dependent on the HIV-1 expressed proteins tat and rev. Productive infection of an MT4-GFP cell with HIV-1 results in GFP expression approximately 24 h post-infection.

MT4-GFP cells were maintained at 37° C./5% $CO_2$/90% relative humidity in RPMI 1640 supplemented with 10% fetal bovine serum, 100 U/ml penicillin/streptomycin, and 400 µg/ml G418 to maintain the reporter gene. For infections, MT4-GFP cells were placed in the same medium lacking G418 and infected overnight with H9IIIB or NL4-3 virus at an approximate multiplicity of infection of 0.01 in the same incubation conditions. Cells were then washed and resuspended in either RPMI 1640 containing no serum at $1.6 \times 10^5$ cells/mL (serum free conditions), 10% normal human serum at $1.6 \times 10^5$ cells/mL (10% NHS conditions) or in 100% normal human serum at $2 \times 10^5$ cells/mL (100% NHS conditions). Compound plates were prepared by dispensing compounds taken up in DMSO into wells of 384 well poly D lysine-coated plates (0.2 µl/well) using an ECHO acoustic dispenser. Each compound was tested in a 10 point serial 3-fold dilution (typical final concentrations: 4.2 µM-0.21 nM). Controls included no inhibitor (DMSO only) and a combination of three antiviral agents (efavirenz, indinavir, and the integrase strand transfer inhibitor L-002254051 at final concentrations of 4 µM each). Cells were added (50 µL/well) to compound plates and the infected cells were maintained at 37° C./5% $CO_2$/90% relative humidity.

Infected cells were quantified at two time points, ~48 h and ~72 h post-infection, by counting the number of green cells in each well using an Acumen eX3 scanner. The increase in the number of green cells over ~24 h period gives the reproductive ratio, $R_0$, which is typically 5-15 and has been shown experimentally to be in logarithmic phase (data not shown). Inhibition of $R_0$ is calculated for each well, and $IC_{50}$ value was determined using non-linear 4-parameter curve fitting.

| Compound | VIKING IP (nM) with 0% NHS | VIKING IP (nM) with 100% NHS |
|---|---|---|
| 2 | 2.8 | 81.1 |
| 4 | 32.2 | 2750 |
| 7 | 0.20 | 2.1 |
| 8 | 2.3 | 660 |
| 9 | 3.8 | 126 |
| 21 | 5.3 | 32.7 |
| 22 | 120 | 340 |
| 23 | 0.28 | 3.6 |
| 24 | 9.1 | 4120 |
| 25 | 190 | 1070 |
| 26 | 1.0 | 35.9 |
| 27 | 5.6 | 78.2 |
| 28 | 221 | 420 |
| 29 | 0.2 | 4.8 |
| 30 | 13.7 | 1050 |
| 31 | 206 | 1070 |
| 32 | 0.9 | 7.0 |
| 33 | 4.4 | 163.0 |
| 34 | 15.4 | 2490.0 |
| 35 | 9.4 | 125.5 |
| 36 | 187.4 | 582.9 |
| 37 | 0.2 | 2.8 |

The present invention is not to be limited by the specific embodiments disclosed in the examples that are intended as illustrations of a few aspects of the invention and any embodiments that are functionally equivalent are within the scope of this invention. Indeed, various modifications of the invention in addition to those shown and described herein will become apparent to those skilled in the art and are intended to fall within the scope of the appended claims.

A number of references have been cited herein, the entire disclosures of which are incorporated herein by reference.

What is claimed is:

1. A compound having the formula:

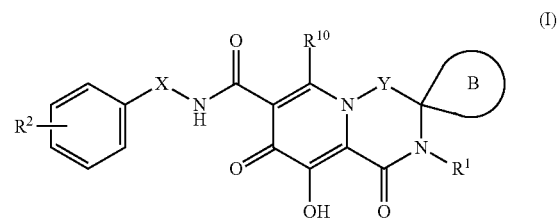

(I)

or a pharmaceutically acceptable salt thereof,
wherein:
B is $C_3$-$C_7$ cycloalkyl, which may be optionally substituted with one or more groups, each independently selected from $R^6$;
X is $C_1$-$C_3$ alkylene;
Y is —$CH_2$—, —$CH(R^6)$— or —$N(R^3)$—;
R is H or benzyl;
$R^1$ is selected from H, $C_1$-$C_6$ alkyl, $C_3$-$C_7$ cycloalkyl, —($C_1$-$C_4$ alkylene)-O—($C_1$-$C_6$ alkyl), —($C_1$-$C_4$ alkylene)-S—($C_1$-$C_6$ alkyl), —($C_1$-$C_4$ alkylene)-$SO_2$—($C_1$-$C_6$ alkyl), —($C_1$-$C_4$ alkylene)-N—($C_1$-$C_6$ alkyl)$_2$, —($C_1$-$C_6$ alkylene)$_m$-Z—($C_1$-$C_3$ alkylene)$_m$-$R^{11}$, $C_1$-$C_6$ haloalkyl, $C_1$-$C_6$ hydroxyalkyl, phenyl, 3 to 8-membered monocyclic heterocycloalkyl and 5 or 6-membered monocyclic heteroaryl;
$R^2$ represents up to 3 optional substituents, each independently selected from halo, $C_1$-$C_6$ alkyl, —O—($C_1$-$C_6$ alkyl) and $C_1$-$C_6$ haloalkyl;
$R^3$ is selected from H, $C_1$-$C_6$ alkyl, —$SO_2R^4$, —C(O)$R^4$, —($C_1$-$C_6$ alkylene)$_p$-C(O)N($R^5$)$_2$, —($C_2$-$C_4$ alkylene)-O—($C_1$-$C_6$ alkyl), —($C_2$-$C_4$ alkylene)-S—($C_1$-$C_6$ alkyl), —($C_2$-$C_4$ alkylene)-$SO_2$—($C_1$-$C_6$ alkyl), —($C_2$-$C_4$ alkylene)-N—($C_1$-$C_6$ alkyl)$_2$, —($C_1$-$C_6$ alkylene)$_m$-Z—($C_1$-$C_3$ alkylene)$_m$-$R^{11}$, $C_3$-$C_7$ cycloalkyl, phenyl, 4 to 8-membered monocyclic heterocycloalkyl or 6-membered monocyclic heteroaryl and 8 to 10-membered bicyclic heteroaryl;
each occurrence of $R^4$ is independently selected from H, $C_1$-$C_6$ alkyl, $C_1$-$C_6$ haloalkyl, $C_3$-$C_7$ cycloalkyl, phenyl, 3 to 8-membered monocyclic heterocycloalkyl, 5 or 6-membered monocyclic heteroaryl and 8 to 10-membered bicyclic heteroaryl, wherein said $C_3$-$C_7$ cycloalkyl group, said phenyl group, said 3 to 8-membered monocyclic heterocycloalkyl group, said 5 or 6-membered monocyclic heteroaryl group and said 8 to 10-membered bicyclic heteroaryl group may be optionally substituted with one or more groups, each independently selected from $R^6$;

each occurrence of $R^5$ is independently selected from H, $C_1$-$C_6$ alkyl, $C_3$-$C_7$ cycloalkyl, —($C_1$-$C_6$ alkylene)-N($R^7$)$_2$, $C_1$-$C_6$ haloalkyl, —C(O)O($C_1$-$C_6$ alkyl), —($C_1$-$C_6$ alkylene)$_m$-Z—($C_1$-$C_3$ alkylene)$_m$-$R^{11}$, —($C_1$-$C_6$ alkylene)$_p$-$R^8$ and —($C_1$-$C_6$ alkylene)-O—($C_1$-$C_6$ alkyl);

each occurrence of $R^6$ is independently selected from halo, $C_1$-$C_6$ alkyl, $C_1$-$C_6$ haloalkyl, —($C_1$-$C_6$ alkylene)$_m$-Z—($C_1$-$C_3$ alkylene)$_m$-$R^{11}$, —N($R^{20}$)$_2$, 3 to 8-membered monocyclic heterocycloalkyl, 6 to 10-membered bicyclic heterocycloalkyl, —O—($C_1$-$C_6$ alkyl), —O—($C_6$-$C_{10}$ aryl), —O—($C_1$-$C_6$ alkylene)-O—($C_1$-$C_6$ alkyl), —O—($C_1$-$C_6$ haloalkyl), —O—($C_1$-$C_6$ alkylene)-O—($C_1$-$C_6$ alkylene)-O—($C_1$-$C_6$ alkyl), —S(O)$_2$($C_1$-$C_6$ alkyl), —NHS(O)$_2$—($C_1$-$C_6$ alkyl), —S(O)$_2$NH—($C_1$-$C_6$ alkyl), —OC(O)—($C_1$-$C_6$ haloalkyl), —($C_1$-$C_6$ alkylene)$_p$-C(O)O—($C_1$-$C_6$ alkyl), —($C_1$-$C_6$ alkylene)$_p$-C(O)—($C_1$-$C_6$ alkyl), —($C_1$-$C_6$ alkylene)$_p$-C(O)N($R^7$)$_2$, $C_1$-$C_6$ hydroxyalkyl, —P(O)(O$R^9$)$_2$, and —CN;

each occurrence of $R^7$ is independently selected from H, $C_1$-$C_6$ alkyl, $C_3$-$C_7$ cycloalkyl, $C_1$-$C_6$ haloalkyl, —C(O)O($C_1$-$C_6$ alkyl), —($C_1$-$C_6$ alkylene)$_m$-Z—($C_1$-$C_3$ alkylene)$_m$-$R^{11}$, —($C_1$-$C_6$ alkylene)$_p$-$R^8$ and —($C_1$-$C_6$ alkylene)-O—($C_1$-$C_6$ alkyl);

each occurrence of $R^8$ is independently selected from H, $C_1$-$C_6$ alkyl, $C_3$-$C_7$ cycloalkyl, 5 or 6-membered monocyclic heteroaryl and 3 to 8-membered monocyclic heterocycloalkyl;

each occurrence of $R^9$ is independently selected from H, $C_1$-$C_6$ alkyl and —($C_1$-$C_6$ alkylene)$_m$-Z—($C_1$-$C_3$ alkylene)$_m$-$R^{11}$;

$R^{10}$ is selected from H, $C_1$-$C_6$ alkyl, $C_3$-$C_7$ cycloalkyl and —($C_1$-$C_4$ alkylene)-O—($C_1$-$C_6$ alkyl);

each occurrence of $R^{11}$ is independently selected from —P(O)(—O$R^{18}$)$_2$,

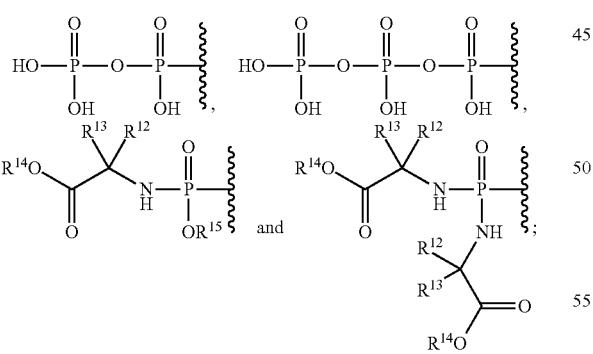

each occurrence of $R^{12}$ is independently selected from H, $C_1$-$C_6$ alkyl, $C_3$-$C_7$ cycloalkyl, phenyl or benzyl, wherein said $C_1$-$C_6$ alkyl may be optionally substituted with a group selected from halo, —O$R^{16}$, —S$R^{16}$, guanidino, —N($R^{16}$)$_2$, —C(O)O$R^{16}$, —C(O)N($R^{16}$)$_2$, —NHC(O)$R^{16}$, 5- or 6-membered monocyclic heteroaryl and 9- or 10-membered bicyclic heteroaryl, and wherein said phenyl group and said benzyl group may be optionally substituted with up to 2 groups, each independently selected from $C_1$-$C_6$ alkyl, halo and —O$R^{16}$;

each occurrence of $R^{13}$ is independently selected from H, $C_1$-$C_6$ alkyl, $C_3$-$C_7$ cycloalkyl, phenyl or benzyl, wherein said $C_1$-$C_6$ alkyl may be optionally substituted with a group selected from halo, —O$R^{16}$, —S$R^{16}$, guanidino, —N($R^{16}$)$_2$, —C(O)O$R^{16}$, —C(O)N($R^{16}$)$_2$, —NHC(O)$R^{16}$, 5- or 6-membered monocyclic heteroaryl and 9- or 10-membered bicyclic heteroaryl, and wherein said phenyl group and said benzyl group may be optionally substituted with up to 2 groups, each independently selected from $C_1$-$C_6$ alkyl, halo and —O$R^{16}$;

each occurrence of $R^{14}$ is independently selected from H, $C_1$-$C_{20}$ alkyl, $C_2$-$C_{20}$ alkenyl, —($C_1$-$C_3$ alkylene)$_m$-($C_3$-$C_7$ cycloalkyl), —($C_1$-$C_3$ alkylene)$_m$-($C_6$-$C_{10}$ aryl) or —($C_1$-$C_3$ alkylene)$_m$-adamantyl, wherein said $C_1$-$C_{20}$ alkyl group, said $C_2$-$C_{20}$ alkenyl group, said $C_6$-$C_{10}$ aryl group and said adamantyl group may be optionally substituted with up to three groups, each independently selected from halo, —O$R^{16}$, —C(O)O$R^{16}$, CN, NO$_2$, $C_1$-$C_6$ haloalkyl, $C_1$-$C_6$ hydroxyalkyl, $C_3$-$C_7$ cycloalkyl, $C_6$-$C_{10}$ aryl, 5- or 6-membered monocyclic heteroaryl, 9- or 10-membered bicyclic heteroaryl, —N($R^{16}$)$_2$, —C(O)N($R^{16}$)$_2$—S$R^{16}$, —S(O)$R^{16}$, —S(O)$_2$$R^{16}$, —S(O)$_2$N($R^{16}$)$_2$, —NHC(O)$R^{16}$, —NHC(O)O$R^{16}$ and —NHC(O)N($R^{16}$)$_2$;

$R^{15}$ is H, $C_6$-$C_{10}$ aryl, 5- or 6-membered monocyclic heteroaryl or 9- or 10-membered bicyclic heteroaryl, wherein said $C_6$-$C_{10}$ aryl group, said 5- or 6-membered monocyclic heteroaryl group and said 9- or 10-membered bicyclic heteroaryl group may be optionally substituted with $R^{17}$;

each occurrence of $R^{16}$ is independently H, $C_1$-$C_{10}$ alkyl, $C_1$-$C_6$ haloalkyl, $C_1$-$C_6$ hydroxyalkyl, —($C_1$-$C_3$ alkylene)$_m$-($C_3$-$C_7$ cycloalkyl), —($C_1$-$C_3$ alkylene)$_m$-($C_6$-$C_{10}$ aryl), —($C_1$-$C_3$ alkylene)$_m$-(4 to 7-membered heterocycloalkyl), —($C_1$-$C_3$ alkylene)$_m$-(5- or 6-membered monocyclic heteroaryl) or —($C_1$-$C_3$ alkylene)$_m$-(9- or 10-membered bicyclic heteroaryl), wherein said $C_3$-$C_7$ cycloalkyl group, said $C_6$-$C_{10}$ aryl group, said 4 to 7-membered heterocycloalkyl group, said -5- or 6-membered monocyclic heteroaryl group or said 9- or 10-membered bicyclic heteroaryl group may be optionally substituted with $R^{17}$;

$R^{17}$ represents from one to five substituent groups, each independently selected from $C_1$-$C_6$ alkyl, halo, —O$R^{19}$, —S$R^{19}$, $C_1$-$C_6$ haloalkyl, $C_1$-$C_6$ hydroxyalkyl, —O—($C_1$-$C_6$ haloalkyl), —CN, —NO$_2$, —N($R^{19}$)$_2$, —C(O)O$R^{19}$, —C(O)N($R^{19}$)$_2$ and —NHC(O)$R^{19}$;

each occurrence of $R^{18}$ is independently selected from H, $C_1$-$C_6$ alkyl, $C_6$-$C_{10}$ aryl, —($C_1$-$C_6$ alkylene)-O—($C_1$-$C_{20}$ alkyl), —($C_1$-$C_6$ alkylene)-O—C(O)—$R^{16}$, and —($C_1$-$C_6$ alkylene)-O—C(O)—O—$R^{16}$;

each occurrence of $R^{19}$ is independently H, $C_1$-$C_{10}$ alkyl, $C_1$-$C_6$ haloalkyl, $C_1$-$C_6$ hydroxyalkyl, —($C_1$-$C_3$ alkylene)$_m$-($C_3$-$C_7$ cycloalkyl), —($C_1$-$C_3$ alkylene)$_m$-($C_6$-$C_{10}$ aryl), —($C_1$-$C_3$ alkylene)$_m$-(4 to 7-membered heterocycloalkyl), —($C_1$-$C_3$ alkylene)$_m$-(5- or 6-membered monocyclic heteroaryl) or —($C_1$-$C_3$ alkylene)$_m$-(9- or 10-membered bicyclic heteroaryl);

each occurrence of $R^{20}$ is independently selected from H, $C_1$-$C_6$ alkyl and —($C_1$-$C_6$ alkylene)$_m$-Z—($C_1$-$C_3$ alkylene)$_m$-$R^{11}$;

each occurrence of Z is independently selected from a bond, —O— or —N($R^9$)—;

each occurrence of m is independently 0 or 1; and each occurrence of p is independently 0 or 1, such that at least one occurrence of $R^{11}$ must be present in the compound of formula (I).

2. The compound of claim 1, wherein X is —CH$_2$—, or a pharmaceutically acceptable salt thereof.

3. The compound of claim 1, wherein $R^{10}$ is H—, or a pharmaceutically acceptable salt thereof.

4. The compound of claim 1, wherein B is cyclopentyl or cyclohexyl, which is optionally substituted with —($C_1$-$C_6$ alkylene)$_m$-$R^{11}$—, or a pharmaceutically acceptable salt thereof.

5. The compound of claim 1, having the formula (Ia):

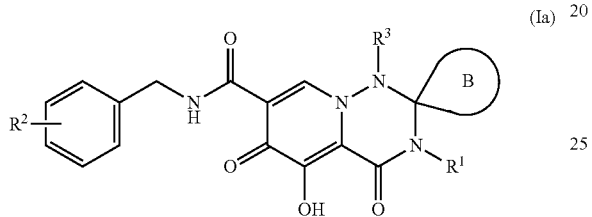

(Ia)

or a pharmaceutically acceptable salt thereof,
wherein:
B is cyclopentyl or cyclohexyl, optionally substituted with $R^6$;
$R^1$ is $C_1$-$C_6$ alkyl or —($C_1$-$C_6$ alkylene)-$R^{11}$;
$R^2$ represents up to 2 optional substituents, each independently selected from halo; and $R^3$ is $C_1$-$C_6$ alkyl or —($C_1$-$C_6$ alkylene)-$R^{11}$;
$R^6$ is —($C_1$-$C_6$ alkylene)$_m$-$R^{11}$;
each occurrence of $R^{11}$ is independently selected from —P(O)(—O$R^{18}$)$_2$ and:

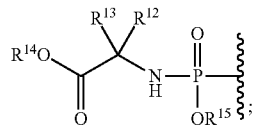

$R^{12}$ is independently selected from H and $C_1$-$C_6$ alkyl;
$R^{13}$ is independently selected from H and $C_1$-$C_6$ alkyl;
$R^{14}$ is $C_1$-$C_6$ alkyl;
$R^{15}$ is $C_6$-$C_{10}$ aryl;
each occurrence of $R^{18}$ is independently selected from H and $C_1$-$C_6$ alkyl; and
m is 0 or 1,
such that at least one occurrence of $R^{11}$ must be present in the compound of formula (I).

6. The compound of claim 1, wherein $R^2$ represents up to 2 optional substituents, each independently selected from halo, or a pharmaceutically acceptable salt thereof.

7. The compound of claim 1, wherein B is substituted with —($C_1$-$C_6$ alkylene)$_m$-$R^{11}$, or a pharmaceutically acceptable salt thereof.

8. The compound of claim 1, wherein $R^3$ is —($C_1$-$C_6$ alkylene)-$R^{11}$, or a pharmaceutically acceptable salt thereof.

9. The compound of claim 1, wherein $R^1$ is methyl or ethyl, or a pharmaceutically acceptable salt thereof.

10. The compound of claim 1, wherein $R^2$ represents two fluoro groups, in the ortho and para positions, or a pharmaceutically acceptable salt thereof.

11. A compound selected from

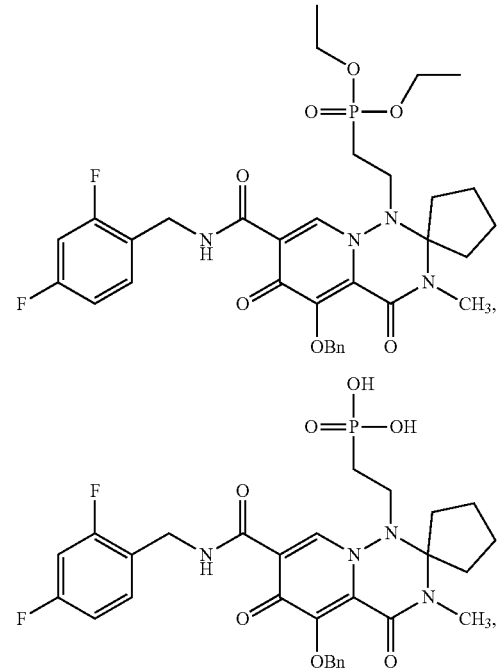

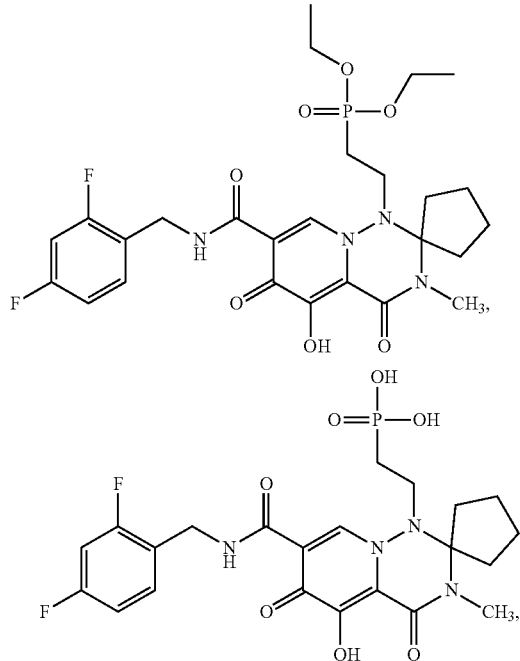

59 60
-continued
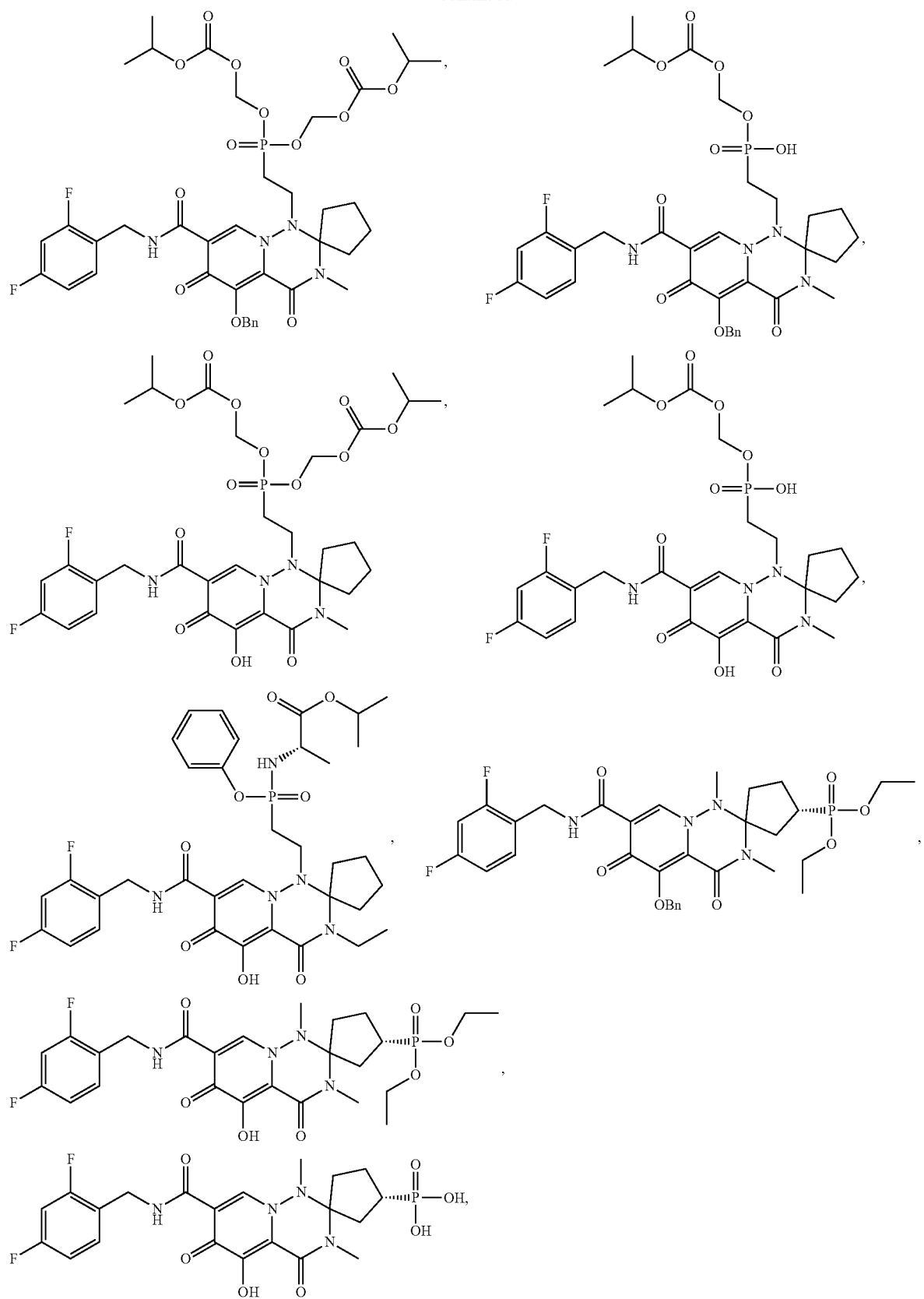

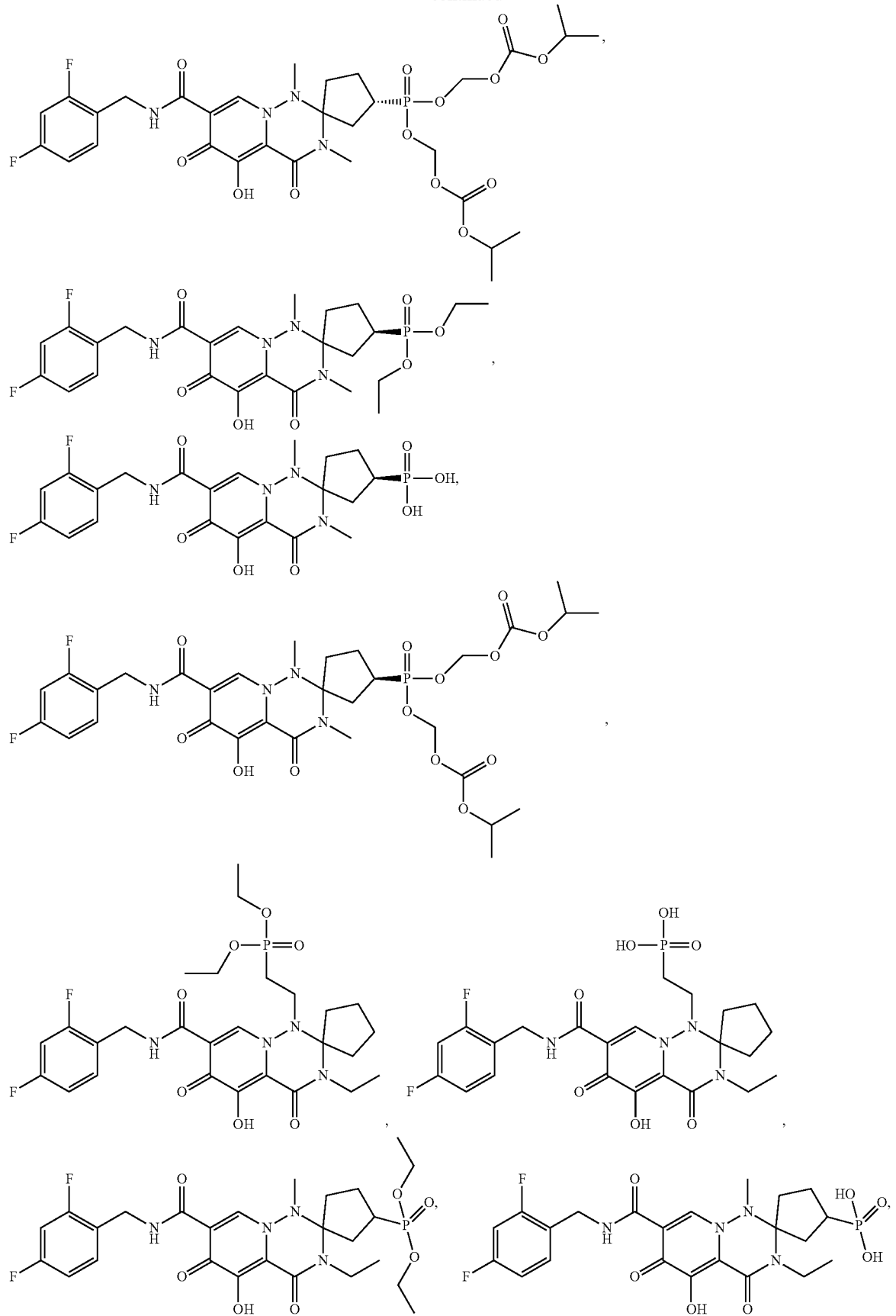

-continued

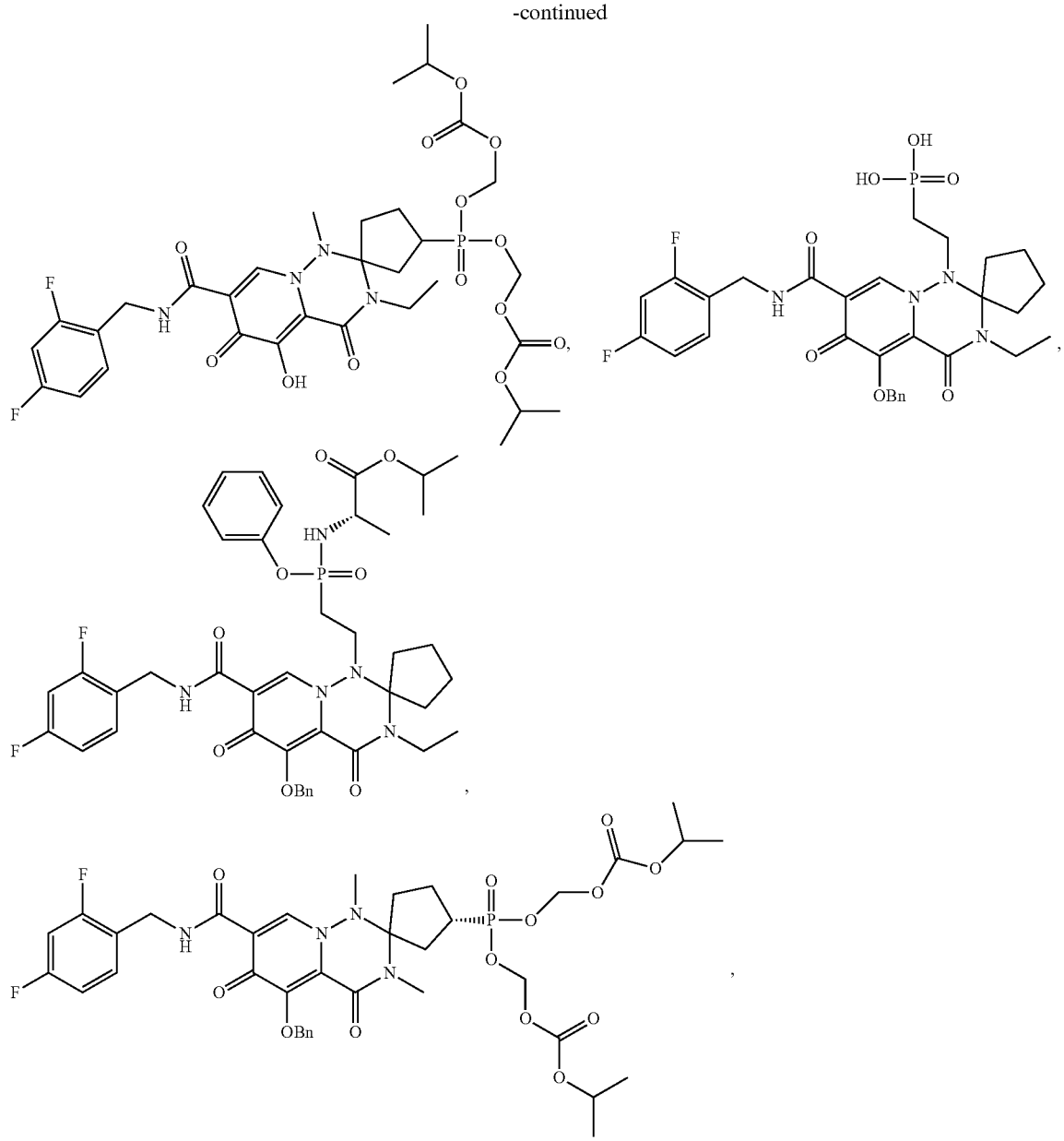

or a pharmaceutically acceptable salt thereof.

12. A pharmaceutical composition comprising an effective amount of a compound according to claim 1, or a pharmaceutically acceptable salt thereof, and a pharmaceutically acceptable carrier.

13. A method for the inhibition of HIV integrase in a subject in need thereof which comprises administering to the subject an effective amount of the compound according to claim 1, or a pharmaceutically acceptable salt thereof.

14. A method for the treatment of infection by HIV or for the treatment, prophylaxis, or delay in the onset or progression of AIDS in a subject in need thereof, which comprises administering to the subject an effective amount of the compound according to claim 1, or a pharmaceutically acceptable salt thereof.

15. The pharmaceutical composition of claim 12, further comprising one or more additional therapeutic agents selected from raltegravir, lamivudine, abacavir, ritonavir, dolutegravir, arunavir, atazanavir, emtricitabine, tenofovir, elvitegravir, rilpivirine and lopinavir.

16. The method of claim 14, further comprising administering to the subject one or more additional therapeutic agents selected from raltegravir, abacavir, lamivudine, ritonavir and lopinavir, wherein the amounts administered of the compounds are together effective to treat infection by HIV or to treat, prevent or delay the onset or progression of AIDS.

* * * * *